(12) United States Patent
Nohr et al.

(10) Patent No.: US 6,294,698 B1
(45) Date of Patent: Sep. 25, 2001

(54) PHOTOINITIATORS AND APPLICATIONS THEREFOR

(75) Inventors: Ronald S. Nohr, Alpharetta; J. Gavin MacDonald, Decatur, both of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/293,162

(22) Filed: Apr. 16, 1999

(51) Int. Cl.$^7$ ................................................ C07C 321/00
(52) U.S. Cl. .......................... 568/21; 568/18; 568/37; 568/38; 568/42; 568/75; 568/77; 522/36; 522/54; 522/55; 522/49
(58) Field of Search .................. 522/36, 54, 55, 522/49; 568/18, 20, 21, 25, 26, 38, 37, 42, 75, 77

(56) References Cited

U.S. PATENT DOCUMENTS

| | | |
|---|---|---|
| Re. 28,225 | 11/1974 | Heseltine et al. . |
| Re. 28,789 | 4/1976 | Chang . |
| 575,228 | * 1/1897 | von Gallois . |
| 582,853 | * 5/1897 | Feer . |
| 893,636 | * 7/1908 | Maywald . |
| 1,013,544 | * 1/1912 | Fuerth . |
| 1,325,971 | * 12/1919 | Akashi . |
| 1,364,406 | * 1/1921 | Olsen . |
| 1,436,856 | * 11/1922 | Brenizer et al. . |
| 1,744,149 | * 1/1930 | Staehlin . |
| 1,803,906 | * 5/1931 | Krieger et al. . |
| 1,844,199 | * 2/1932 | Bicknell et al. . |
| 1,876,880 | * 9/1932 | Drapal . |
| 1,880,572 | * 10/1932 | Wendt et al. . |
| 1,880,573 | * 10/1932 | Wendt et al. . |
| 1,916,350 | * 7/1933 | Wendt et al. . |
| 1,916,779 | * 7/1933 | Wendt et al. . |
| 1,955,898 | * 4/1934 | Wendt et al. . |
| 1,962,111 | * 6/1934 | Bamberger . |
| 2,005,378 | 6/1935 | Kiel . |
| 2,005,511 | * 6/1935 | Stoll et al. . |
| 2,049,005 | 7/1936 | Gaspar . |
| 2,054,390 | 9/1936 | Rust et al. . |
| 2,058,489 | 10/1936 | Murch et al. . |
| 2,062,304 | 12/1936 | Gaspar . |

(List continued on next page.)

FOREIGN PATENT DOCUMENTS

| | | |
|---|---|---|
| 12624/88 | 9/1988 | (AU) . |
| 620075 | 5/1962 | (BE) . |
| 637169 | 3/1964 | (BE) . |
| 413257 | 10/1932 | (CA) . |
| 458808 | 12/1936 | (CA) . |
| 537687 | 3/1957 | (CA) . |
| 552565 | 2/1958 | (CA) . |
| 571792 | 3/1959 | (CA) . |
| 779239 | 2/1968 | (CA) . |
| 930103 | 7/1973 | (CA) . |
| 2053094 | 4/1992 | (CA) . |
| 603767 | 8/1978 | (CH) . |
| 197808 | 5/1988 | (CH) . |
| 94118 | 5/1958 | (CS) . |
| 1047787 | 12/1957 | (DE) . |
| 1022801 | 1/1958 | (DE) . |
| 1039835 | 9/1958 | (DE) . |
| 1040562 | 10/1958 | (DE) . |
| 1045414 | 12/1958 | (DE) . |
| 1047013 | 12/1958 | (DE) . |
| 1132540 | 7/1962 | (DE) . |
| 1154069 | 9/1963 | (DE) . |
| 1240811 | 5/1967 | (DE) . |
| 2202497 | 8/1972 | (DE) . |
| 2432563 | 2/1975 | (DE) . |

(List continued on next page.)

OTHER PUBLICATIONS

Noguchi, H., UV Curable, Aqueous Ink Jet Ink: Material Design and Performance for Digital Printing, *1998 International Conf. on Digital Printing Technologies*, 107–110, 1998.

ESP@CENET databse, JP 10324836 (Omron Corp.), Dec. 8, 1998. abstract, 1998.

Derwent World Patents Index, JP 8002092 (Mitsubishi Paper Mills Ltd.) Jan. 9, 1996. abstract, 1996.

Kubat et al., "Photophysical properties of metal complexes of meso–tetrakis (40sulphonatophenyl) porphyrin," *J. Photochem. and Photobiol.*, 96, 93–97, 1996.

Derwent World Patents Index, EP 659039 (Canon KK) Jun. 21, 1995. abstract, 1995.

Derwent World Patents Index, JP 7061114 (Dainippon Printing Co. Ltd.) Mar. 7, 1995. abstract, 1995.

Abstract for WO 95/00343–A1, *Textiles: Paper: Cellulose*, p. 7, 1995.

Maki, Y. et al., "A novel heterocyclic N–oxide, pyrimido[5,4–g]pteridinetetrone 5–oxide, with multifunctional photo-oxidative properties", *Chemical Abstracts*, 122, 925 [No. 122:31350F], 1995.

Abstract of patent, JP 6–80915 (Canon Inc.), Mar. 22, 1994. 1994.

Abstract of patent, JP 06–43573 (Iku Meji) (Feb. 18, 1994), 1994.

Pitchumani, K. et al., "Modification of chemical reactivity upon cyclodextrin encapsulation", *Chemical Abstracts*, 121, 982 [No. 121:133624v], 1994.

(List continued on next page.)

*Primary Examiner*—James J. Seidleck
*Assistant Examiner*—Sanza L. McClendon
(74) *Attorney, Agent, or Firm*—Jones & Askew, LLP

(57) ABSTRACT

The present invention is directed to new, energy-efficient photoinitiators in the form of organic sulfur-containing compounds. The present invention is also directed to a method of generating reactive species which includes exposing one or more photoinitiators to radiation to form one or more reactive species. Also described are methods of polymerizing unsaturated monomers, methods of curing an unsaturated oligomer/monomer mixture, and methods of laminating using the photoinitiators of the present invention.

25 Claims, No Drawings

U.S. PATENT DOCUMENTS

| | | |
|---|---|---|
| 2,090,511 | 8/1937 | Crossley et al. . |
| 2,097,119 | 10/1937 | Eggert . |
| 2,106,539 | 1/1938 | Schnitzspahn . |
| 2,111,692 | 3/1938 | Saunders et al. . |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. . |
| 2,154,996 | 4/1939 | Rawling . |
| 2,159,280 | 5/1939 | Mannes et al. . |
| 2,171,976 | 9/1939 | Erickson . |
| 2,181,800 | 11/1939 | Crossley et al. . |
| 2,185,153 | 12/1939 | Lecher et al. . |
| 2,220,178 | 11/1940 | Schneider . |
| 2,230,590 | 2/1941 | Eggert et al. . |
| 2,237,885 | 4/1941 | Markush et al. . |
| 2,243,630 | 5/1941 | Houk et al. . |
| 2,268,324 | 12/1941 | Polgar . |
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,580,461 | 1/1952 | Pearl . |
| 2,601,669 * | 6/1952 | Tullsen . |
| 2,612,494 * | 9/1952 | von Glahn et al. . |
| 2,612,495 * | 9/1952 | von Glahn et al. . |
| 2,628,959 * | 2/1953 | von Glahn et al. . |
| 2,647,080 * | 7/1953 | Joyce . |
| 2,680,685 * | 6/1954 | Ratchford . |
| 2,728,784 * | 12/1955 | Tholstrup et al. . |
| 2,732,301 * | 1/1956 | Robertson et al. . |
| 2,744,103 * | 5/1956 | Koch . |
| 2,757,090 * | 7/1956 | Meugebauer et al. . |
| 2,763,550 * | 9/1956 | Lovick . |
| 2,768,171 * | 10/1956 | Clarke et al. . |
| 2,773,056 * | 12/1956 | Helfaer . |
| 2,798,000 * | 7/1957 | Monterman . |
| 2,809,189 * | 10/1957 | Stanley et al. . |
| 2,827,358 * | 3/1958 | Kaplan et al. . |
| 2,834,773 * | 5/1958 | Scalera et al. . |
| 2,875,045 * | 2/1959 | Lurie . |
| 2,892,865 * | 6/1959 | Giraldi et al. . |
| 2,897,187 | 7/1959 | Koch . |
| 2,936,241 | 5/1960 | Sharp et al. . |
| 2,940,853 | 6/1960 | Sagura et al. . |
| 2,955,067 | 10/1960 | McBurney et al. . |
| 2,992,129 | 7/1961 | Gauthier . |
| 2,992,198 | 7/1961 | Funahashi . |
| 3,030,208 | 4/1962 | Schellenberg et al. . |
| 3,071,815 | 1/1963 | MacKinnon . |
| 3,075,014 | 1/1963 | Palopoli et al. . |
| 3,076,813 | 2/1963 | Sharp . |
| 3,104,973 | 9/1963 | Sprague et al. . |
| 3,114,634 | 12/1963 | Brown et al. . |
| 3,121,632 | 2/1964 | Sprague et al. . |
| 3,123,647 | 3/1964 | Duennenberger et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 * | 4/1965 | Anderau et al. . |
| 3,238,163 * | 3/1966 | O'Neill . |
| 3,242,215 * | 3/1966 | Heitmiller . |
| 3,248,337 * | 4/1966 | Zirker et al. . |
| 3,266,973 * | 8/1966 | Crowley . |
| 3,282,886 * | 11/1966 | Gadecki . |
| 3,284,205 * | 11/1966 | Sprague et al. . |
| 3,300,314 * | 1/1967 | Rauner et al. . |
| 3,304,297 * | 2/1967 | Wegmann et al. . |
| 3,305,361 * | 2/1967 | Gaynor et al. . |
| 3,313,797 * | 4/1967 | Kissa . |
| 3,320,080 * | 5/1967 | Mazzarella et al. . |
| 3,330,659 * | 7/1967 | Wainer . |
| 3,341,492 * | 9/1967 | Champ et al. . |
| 3,359,109 * | 12/1967 | Harder et al. . |
| 3,361,827 * | 1/1968 | Biletch . |
| 3,363,969 * | 1/1968 | Brooks . |
| 3,385,700 * | 5/1968 | Willems et al. . |
| 3,397,984 * | 8/1968 | Williams et al. . |
| 3,415,875 | 12/1968 | Luethi et al. . |
| 3,418,118 | 12/1968 | Thommes et al. . |
| 3,445,234 | 5/1969 | Cescon et al. . |
| 3,453,258 | 7/1969 | Parmerter et al. . |
| 3,453,259 | 7/1969 | Parmerter et al. . |
| 3,464,841 | 9/1969 | Skofronick . |
| 3,467,647 | 9/1969 | Benninga . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,541,142 | 11/1970 | Cragoe, Jr. . |
| 3,546,161 | 12/1970 | Wolheim . |
| 3,547,646 | 12/1970 | Hori et al. . |
| 3,549,367 | 12/1970 | Chang et al. . |
| 3,553,710 | 1/1971 | Lloyd et al. . |
| 3,563,931 | 2/1971 | Horiguchi ............... 260/41 |
| 3,565,753 | 2/1971 | Yurkowitz . |
| 3,574,624 | 4/1971 | Reynolds et al. . |
| 3,579,533 | 5/1971 | Yalman . |
| 3,595,655 | 7/1971 | Robinson et al. .............. 96/48 |
| 3,595,657 | 7/1971 | Robinson et al. .............. 96/48 |
| 3,595,658 | 7/1971 | Gerlach et al. .............. 96/48 |
| 3,595,659 | 7/1971 | Gerlach et al. .............. 96/48 |
| 3,607,639 | 9/1971 | Krefeld et al. . |
| 3,607,693 | 9/1971 | Heine et al. ............ 204/159.15 |
| 3,607,863 | 9/1971 | Dosch . |
| 3,615,562 | 10/1971 | Harrison et al. .............. 96/89 |
| 3,617,288 | 11/1971 | Hartman et al. . |
| 3,617,335 | 11/1971 | Kumura et al. . |
| 3,619,238 | 11/1971 | Kimura et al. . |
| 3,619,239 | 11/1971 | Osada et al. . |
| 3,637,337 | 1/1972 | Pilling . |
| 3,637,581 | 1/1972 | Horioguchi et al. ............ 260/41.5 R |
| 3,642,472 | 2/1972 | Mayo ............... 63/24 |
| 3,647,467 | 3/1972 | Grubb ............... 96/90 |
| 3,652,275 | 3/1972 | Baum et al. . |
| 3,660,542 | 5/1972 | Adachi et al. . |
| 3,667,954 | 6/1972 | Itano et al. .............. 96/90 |
| 3,668,188 | 6/1972 | King et al. . |
| 3,669,925 | 6/1972 | King et al. . |
| 3,671,096 | 6/1972 | Mackin ............... 350/3.5 |
| 3,671,251 | 6/1972 | Houle et al. .............. 96/89 |
| 3,676,690 | 7/1972 | McMillin et al. . |
| 3,678,044 | 7/1972 | Adams . |
| 3,689,565 | 9/1972 | Hoffmann et al. . |
| 3,694,241 | 9/1972 | Guthrie et al. . |
| 3,695,879 | 10/1972 | Laming et al. .............. 96/48 |
| 3,697,280 | 10/1972 | Strilko ............... 96/90 |
| 3,705,043 | 12/1972 | Zablak . |
| 3,707,371 | 12/1972 | Files ............... 96/27 |

| | | | | | | | |
|---|---|---|---|---|---|---|---|
| 3,729,313 | 4/1973 | Smith | 96/27 | 4,239,843 | 12/1980 | Hara et al. | 430/17 |
| 3,737,628 | 6/1973 | Azure . | | 4,239,850 | 12/1980 | Kita et al. . | |
| 3,765,896 | 10/1973 | Fox | 96/89 | 4,241,155 | 12/1980 | Hara et al. | 430/17 |
| 3,775,130 | 11/1973 | Enomoto et al. | 96/90 | 4,242,430 | 12/1980 | Hara et al. | 430/17 |
| 3,788,849 | 1/1974 | Taguchi et al. | 96/48 | 4,242,431 | 12/1980 | Hara et al. | 430/17 |
| 3,799,773 | 3/1974 | Watarai et al. . | | 4,245,018 | 1/1981 | Hara et al. | 430/14 |
| 3,800,439 | 4/1974 | Sokolski et al. . | | 4,245,033 | 1/1981 | Eida et al. . | |
| 3,801,329 | 4/1974 | Sandner et al. . | | 4,245,995 | 1/1981 | Hugl et al. . | |
| 3,817,752 | 6/1974 | Laridon et al. . | | 4,246,330 | 1/1981 | Hara et al. | 430/17 |
| 3,840,338 | 10/1974 | Zviak et al. . | | 4,248,949 | 2/1981 | Hara et al. | 430/17 |
| 3,844,790 | 10/1974 | Chang et al. . | | 4,250,096 | 2/1981 | Kvita et al. . | |
| 3,870,524 | 3/1975 | Watanabe et al. | 96/115 P | 4,251,622 | 2/1981 | Kimoto et al. . | |
| 3,873,500 | 3/1975 | Kato et al. . | | 4,251,662 | 2/1981 | Ozawa et al. . | |
| 3,876,496 | 4/1975 | Lozano . | | 4,254,195 | 3/1981 | Hara et al. | 430/17 |
| 3,887,450 | 6/1975 | Gilano et al. | 204/159.15 | 4,256,493 | 3/1981 | Yokoyama et al. . | |
| 3,895,949 | 7/1975 | Akamatsu | 96/86 P | 4,256,817 | 3/1981 | Hara et al. | 430/17 |
| 3,901,779 | 8/1975 | Mani | 204/159.16 | 4,258,123 | 3/1981 | Nagashima et al. . | |
| 3,904,562 | 9/1975 | Hopfenberg et al. . | | 4,258,367 | 3/1981 | Mansukhani . | |
| 3,910,993 | 10/1975 | Avar et al. . | | 4,259,432 | 3/1981 | Kondoh et al. . | |
| 3,914,165 | 10/1975 | Gaske | 204/159.15 | 4,262,936 | 4/1981 | Miyamoto . | |
| 3,914,166 | 10/1975 | Rudolph et al. | 204/159.15 | 4,268,605 | 5/1981 | Hara et al. | 430/216 |
| 3,915,824 | 10/1975 | McGinniss . | | 4,268,667 | 5/1981 | Anderson . | |
| 3,919,323 | 11/1975 | Houlihan et al. . | | 4,269,926 | 5/1981 | Hara et al. | 430/216 |
| 3,926,641 | 12/1975 | Rosen . | | 4,270,130 | 5/1981 | Houle et al. . | |
| 3,928,264 | 12/1975 | Young, Jr. et al. | 96/115 P | 4,271,252 | 6/1981 | Hara et al. | 430/216 |
| 3,933,682 | 1/1976 | Bean . | | 4,271,253 | 6/1981 | Hara et al. | 430/216 |
| 3,952,129 | 4/1976 | Matsukawa et al. . | | 4,272,244 | 6/1981 | Schlick . | |
| 3,960,685 | 6/1976 | Sano et al. . | | 4,276,211 | 6/1981 | Singer et al. . | |
| 3,965,157 | 6/1976 | Harrison . | | 4,277,497 | 7/1981 | Fromantin . | |
| 3,978,132 | 8/1976 | Houlihan et al. . | | 4,279,653 | 7/1981 | Makishima et al. . | |
| 3,984,248 | 10/1976 | Sturmer . | | 4,279,982 | 7/1981 | Iwasaki et al. . | |
| 3,988,154 | 10/1976 | Sturmer . | | 4,279,985 | 7/1981 | Nonogaki et al. . | |
| 4,004,998 | 1/1977 | Rosen . | | 4,284,485 | 8/1981 | Berner . | |
| 4,012,256 | 3/1977 | Levinos . | | 4,288,631 | 9/1981 | Ching . | |
| 4,017,652 | 4/1977 | Gruber . | | 4,289,844 | 9/1981 | Specht et al. . | |
| 4,022,674 | 5/1977 | Rosen . | | 4,290,870 | 9/1981 | Kondoh et al. . | |
| 4,024,324 | 5/1977 | Sparks . | | 4,293,458 | 10/1981 | Gruenberger et al. . | |
| 4,039,332 | 8/1977 | Kokelenberg et al. . | | 4,298,679 | 11/1981 | Shinozaki et al. . | |
| 4,043,819 | 8/1977 | Baumann . | | 4,300,123 | 11/1981 | McMillin et al. . | |
| 4,048,034 | 9/1977 | Martan . | | 4,301,223 | 11/1981 | Nakamura et al. | 430/17 |
| 4,054,719 | 10/1977 | Cordes, III . | | 4,302,606 | 11/1981 | Barabas et al. . | |
| 4,056,665 | 11/1977 | Tayler et al. . | | 4,306,014 | 12/1981 | Kunikane et al. . | |
| 4,058,400 | 11/1977 | Crivello . | | 4,307,182 | 12/1981 | Dalzell et al. . | |
| 4,067,892 | 1/1978 | Thorne et al. . | | 4,308,400 | 12/1981 | Felder et al. . | |
| 4,071,424 | 1/1978 | Dart et al. . | | 4,315,807 | 2/1982 | Felder et al. . | |
| 4,073,968 | 2/1978 | Miyamoto et al. . | | 4,318,705 | 3/1982 | Nowak et al. . | |
| 4,077,769 | 3/1978 | Garcia . | | 4,318,791 | 3/1982 | Felder et al. . | |
| 4,079,183 | 3/1978 | Green . | | 4,321,118 | 3/1982 | Felder et al. . | |
| 4,085,062 | 4/1978 | Virgilio et al. . | | 4,335,054 | 6/1982 | Blaser et al. . | |
| 4,090,877 | 5/1978 | Streeper . | | 4,335,055 | 6/1982 | Blaser et al. . | |
| 4,100,047 | 7/1978 | McCarty . | | 4,336,323 | 6/1982 | Winslow . | |
| 4,105,572 | 8/1978 | Gorondy . | | 4,343,891 | 8/1982 | Aasen et al. . | |
| 4,107,733 | 8/1978 | Schickedanz . | | 4,345,011 | 8/1982 | Drexhage . | |
| 4,110,112 | 8/1978 | Roman et al. . | | 4,347,111 | 8/1982 | Gehlhaus et al. . | |
| 4,111,699 | 9/1978 | Krueger . | | 4,349,617 | 9/1982 | Kawashiri et al. . | |
| 4,114,028 | 9/1978 | Baio et al. . | | 4,350,753 | 9/1982 | Shelnut et al. . | |
| 4,126,412 | 11/1978 | Masson et al. . | | 4,351,893 | 9/1982 | Anderson . | |
| 4,132,562 | 1/1979 | Burke, Jr. et al. . | | 4,356,255 | 10/1982 | Tachikawa et al. . | |
| 4,141,807 | 2/1979 | Via . | | 4,357,468 | 11/1982 | Szejtli et al. . | |
| 4,144,156 | 3/1979 | Kuesters et al. . | | 4,359,524 | 11/1982 | Masuda et al. . | |
| 4,148,658 | 4/1979 | Kondoh et al. . | | 4,362,806 | 12/1982 | Whitmore . | |
| 4,162,162 | 7/1979 | Dueber . | | 4,367,072 | 1/1983 | Vogtle et al. . | |
| 4,171,977 | 10/1979 | Hasegawa et al. . | | 4,367,280 | 1/1983 | Kondo et al. . | |
| 4,179,577 | 12/1979 | Green . | | 4,369,283 | 1/1983 | Altschuler . | |
| 4,181,807 | 1/1980 | Green . | | 4,370,401 | 1/1983 | Winslow et al. . | |
| 4,190,671 | 2/1980 | Vanstone et al. . | | 4,372,582 | 2/1983 | Geisler . | |
| 4,197,080 | 4/1980 | Mee . | | 4,373,017 | 2/1983 | Masukawa et al. . | |
| 4,199,420 | 4/1980 | Photis . | | 4,373,020 | 2/1983 | Winslow . | |
| 4,229,172 | 10/1980 | Baumann et al. . | | 4,374,984 | 2/1983 | Eichler et al. . | |
| 4,232,106 | 11/1980 | Iwasaki et al. . | | 4,376,887 | 3/1983 | Greenaway et al. . | |
| 4,238,492 | 12/1980 | Majoie . | | 4,383,835 | 5/1983 | Preuss et al. . | |

| | | | | | | |
|---|---|---|---|---|---|---|
| 4,390,616 | 6/1983 | Sato et al. . | | 4,727,824 | 3/1988 | Ducharme et al. . |
| 4,391,867 | 7/1983 | Derick et al. . | | 4,732,615 | 3/1988 | Kawashita et al. . |
| 4,399,209 | 8/1983 | Sanders et al. . | | 4,737,190 | 4/1988 | Shimada et al. . |
| 4,400,173 | 8/1983 | Beavan . | | 4,737,438 | 4/1988 | Ito et al. . |
| 4,401,470 | 8/1983 | Bridger . | | 4,740,451 | 4/1988 | Kohara . |
| 4,416,961 | 11/1983 | Drexhage . | | 4,745,042 | 5/1988 | Sasago et al. . |
| 4,421,559 | 12/1983 | Owatari . | | 4,746,735 | 5/1988 | Kruper, Jr. et al. . |
| 4,424,325 | 1/1984 | Tsunoda et al. . | | 4,752,341 | 6/1988 | Rock . |
| 4,425,162 | 1/1984 | Sugiyama . | | 4,755,450 | 7/1988 | Sanders et al. . |
| 4,425,424 | 1/1984 | Altland et al. . | | 4,761,181 | 8/1988 | Suzuki . |
| 4,426,153 | 1/1984 | Libby et al. . | | 4,766,050 | 8/1988 | Jerry . |
| 4,434,035 | 2/1984 | Eichler et al. . | | 4,766,055 | 8/1988 | Kawabata et al. . |
| 4,440,827 | 4/1984 | Miyamoto et al. . | | 4,770,667 | 9/1988 | Evans et al. . |
| 4,447,521 | 5/1984 | Tiers et al. . | | 4,772,291 | 9/1988 | Shibanai et al. . |
| 4,450,227 | 5/1984 | Holmes et al. . | | 4,772,541 | 9/1988 | Gottschalk . |
| 4,460,676 | 7/1984 | Fabel . | | 4,775,386 | 10/1988 | Reinert et al. . |
| 4,467,112 | 8/1984 | Matsuura et al. . | | 4,786,586 | 11/1988 | Lee et al. . |
| 4,475,999 | 10/1984 | Via . | | 4,789,382 | 12/1988 | Neumann et al. . |
| 4,477,681 | 10/1984 | Gehlhaus et al. . | | 4,790,565 | 12/1988 | Steed . |
| 4,489,334 | 12/1984 | Owatari . | | 4,800,149 | 1/1989 | Gottschalk . |
| 4,495,041 | 1/1985 | Goldstein . | | 4,803,008 | 2/1989 | Ciolino et al. . |
| 4,496,447 | 1/1985 | Eichler et al. . | | 4,808,189 | 2/1989 | Oishi et al. . |
| 4,500,355 | 2/1985 | Shimada et al. . | | 4,812,139 | 3/1989 | Brodmann . |
| 4,508,570 | 4/1985 | Fugii et al. . | | 4,812,517 | 3/1989 | West ........................................ 525/94 |
| 4,510,392 | 4/1985 | Litt et al. . | | 4,813,970 | 3/1989 | Kirjanov et al. . |
| 4,523,924 | 6/1985 | Lacroix . | | 4,822,714 | 4/1989 | Sanders . |
| 4,524,122 | 6/1985 | Weber et al. . | | 4,831,068 | 5/1989 | Reinert et al. . |
| 4,534,838 | 8/1985 | Lin et al. . | | 4,834,771 | 5/1989 | Yamauchi et al. . |
| 4,548,896 | 10/1985 | Sabongi et al. . | | 4,837,106 | 6/1989 | Ishikawa et al. . |
| 4,555,474 | 11/1985 | Kawamura . | | 4,837,331 | 6/1989 | Yamanishi et al. . |
| 4,557,730 | 12/1985 | Bennett et al. . | | 4,838,938 | 6/1989 | Tomida et al. . |
| 4,564,560 | 1/1986 | Tani et al. . | | 4,839,269 | 6/1989 | Okazaki et al. . |
| 4,565,769 | 1/1986 | Dueber et al. . | | 4,849,320 | 7/1989 | Irving et al. . |
| 4,567,171 | 1/1986 | Mangum . | | 4,853,037 | 8/1989 | Johnson et al. . |
| 4,571,377 | 2/1986 | McGinniss et al. . | | 4,853,398 | 8/1989 | Carr et al. . |
| 4,595,745 | 6/1986 | Nakano et al. . | | 4,854,971 | 8/1989 | Gane et al. . |
| 4,604,344 | 8/1986 | Irving et al. . | | 4,857,438 | 8/1989 | Loerzer et al. . |
| 4,605,442 | 8/1986 | Kawashita et al. . | | 4,861,916 | 8/1989 | Kohler et al. . |
| 4,613,334 | 9/1986 | Thomas et al. ........................ 8/442 | | 4,865,942 | 9/1989 | Gottschalk et al. . |
| 4,614,723 | 9/1986 | Schmidt et al. . | | 4,874,391 | 10/1989 | Reinert . |
| 4,617,380 | 10/1986 | Hinson et al. . | | 4,874,899 | 10/1989 | Hoelderich et al. . |
| 4,620,875 | 11/1986 | Shimada et al. . | | 4,885,395 | 12/1989 | Hoelderich . |
| 4,620,876 | 11/1986 | Fugii et al. . | | 4,886,774 | 12/1989 | Doi . |
| 4,622,286 | 11/1986 | Sheets . | | 4,892,941 | 1/1990 | Dolphin et al. . |
| 4,631,085 | 12/1986 | Kawanishi et al. . | | 4,895,880 | 1/1990 | Gottschalk . |
| 4,632,891 | 12/1986 | Banks et al. . | | 4,900,581 | 2/1990 | Stuke et al. . |
| 4,632,895 | 12/1986 | Patel et al. . | | 4,902,299 | 2/1990 | Anton . |
| 4,634,644 | 1/1987 | Irving et al. . | | 4,902,725 | 2/1990 | Moore . |
| 4,638,340 | 1/1987 | Iiyama et al. . | | 4,902,787 | 2/1990 | Freeman . |
| 4,647,310 | 3/1987 | Shimada et al. . | | 4,911,732 | 3/1990 | Neumann et al. . |
| 4,655,783 | 4/1987 | Reinert et al. . | | 4,911,899 | 3/1990 | Hagiwara et al. . |
| 4,663,275 | 5/1987 | West et al. . | | 4,917,956 | 4/1990 | Rohrbach . |
| 4,663,641 | 5/1987 | Iiyama et al. . | | 4,921,317 | 5/1990 | Suzuki et al. . |
| 4,668,533 | 5/1987 | Miller . | | 4,925,770 | 5/1990 | Ichiura et al. . |
| 4,672,041 | 6/1987 | Jain . | | 4,925,777 | 5/1990 | Inoue et al. . |
| 4,698,291 | 10/1987 | Koibuchi et al. . | | 4,926,190 | 5/1990 | Lavar . |
| 4,701,402 | 10/1987 | Patel et al. . | | 4,933,265 | 6/1990 | Inoue et al. . |
| 4,702,996 | 10/1987 | Griffing et al. . | | 4,933,948 | 6/1990 | Herkstroeter . |
| 4,704,133 | 11/1987 | Reinert et al. . | | 4,937,161 | 6/1990 | Kita et al. . |
| 4,707,161 | 11/1987 | Thomas et al. ........................ 8/442 | | 4,942,113 | 7/1990 | Trundle . |
| 4,707,425 | 11/1987 | Sasagawa et al. ........................ 8/44 | | 4,944,988 | 7/1990 | Yasuda et al. . |
| 4,707,430 | 11/1987 | Ozawa et al. . | | 4,950,304 | 8/1990 | Reinert et al. . |
| 4,711,668 | 12/1987 | Shimada et al. . | | 4,952,478 | 8/1990 | Miyagawa et al. . |
| 4,711,802 | 12/1987 | Tannenbaum . | | 4,952,680 | 8/1990 | Schmeidl . |
| 4,713,113 | 12/1987 | Shimada et al. . | | 4,954,380 | 9/1990 | Kanome et al. . |
| 4,720,450 | 1/1988 | Ellis . | | 4,954,416 | 9/1990 | Wright et al. . |
| 4,721,531 | 1/1988 | Wildeman et al. ................. 106/309 | | 4,956,254 | 9/1990 | Washizu et al. . |
| 4,721,734 | 1/1988 | Gehlhaus et al. . | | 4,964,871 | 10/1990 | Reinert et al. . |
| 4,724,021 | 2/1988 | Martin et al. . | | 4,965,294 | 10/1990 | Ohnegemach et al. . |
| 4,724,201 | 2/1988 | Okazaki et al. . | | 4,966,607 | 10/1990 | Shinoki et al. . |
| 4,725,527 | 2/1988 | Robillard . | | 4,966,833 | 10/1990 | Inoue . |

| | | |
|---|---|---|
| 4,968,596 | 11/1990 | Inoue et al. . |
| 4,968,813 | 11/1990 | Rule et al. . |
| 4,985,345 | 1/1991 | Hayakawa et al. . |
| 4,987,056 | 1/1991 | Imahashi et al. . |
| 4,988,561 | 1/1991 | Wason . |
| 4,997,745 | 3/1991 | Kawamura et al. . |
| 5,001,330 | 3/1991 | Koch . |
| 5,002,853 | 3/1991 | Aoai et al. . |
| 5,002,993 | 3/1991 | West et al. . |
| 5,003,142 | 3/1991 | Fuller . |
| 5,006,758 | 4/1991 | Gellert et al. . |
| 5,013,959 | 5/1991 | Kogelschatz . |
| 5,017,195 | 5/1991 | Satou et al. . |
| 5,023,129 | 6/1991 | Morganti et al. . |
| 5,025,036 | 6/1991 | Carson et al. . |
| 5,026,425 | 6/1991 | Hindagolla et al. . |
| 5,026,427 | 6/1991 | Mitchell et al. . |
| 5,028,262 | 7/1991 | Barlow, Jr. et al. . |
| 5,028,792 | 7/1991 | Mullis . |
| 5,030,243 | 7/1991 | Reinert . |
| 5,030,248 | 7/1991 | Meszaros . |
| 5,034,526 | 7/1991 | Bonham et al. . |
| 5,037,726 | 8/1991 | Kojima et al. . |
| 5,045,435 | 9/1991 | Adams et al. . |
| 5,045,573 | 9/1991 | Kohler et al. . |
| 5,047,556 | 9/1991 | Kohler et al. . |
| 5,049,777 | 9/1991 | Mechtersheimer . |
| 5,053,320 | 10/1991 | Robbillard . |
| 5,055,579 | 10/1991 | Pawlowski et al. . |
| 5,057,562 | 10/1991 | Reinert . |
| 5,068,140 | 11/1991 | Malhotra et al. . |
| 5,068,364 | 11/1991 | Takagaki et al. . |
| 5,069,681 | 12/1991 | Bouwknegt et al. . |
| 5,070,001 | 12/1991 | Stahlhofen . |
| 5,073,448 | 12/1991 | Vieira et al. . |
| 5,074,885 | 12/1991 | Reinert . |
| 5,076,808 | 12/1991 | Hahn et al. . |
| 5,085,698 | 2/1992 | Ma et al. . |
| 5,087,550 | 2/1992 | Blum et al. . |
| 5,089,050 | 2/1992 | Vieira et al. . |
| 5,089,374 | 2/1992 | Saeva . |
| 5,096,456 | 3/1992 | Reinert et al. . |
| 5,096,489 | 3/1992 | Laver ........................................ 106/20 |
| 5,096,781 | 3/1992 | Vieira et al. ...................... 428/411.1 |
| 5,098,477 | 3/1992 | Vieira et al. . |
| 5,098,793 | 3/1992 | Rohrbach et al. . |
| 5,098,806 | 3/1992 | Robillard . |
| 5,106,723 | 4/1992 | West et al. . |
| 5,108,505 | 4/1992 | Moffat . |
| 5,108,874 | 4/1992 | Griffing et al. . |
| 5,110,706 | 5/1992 | Yumoto et al. . |
| 5,110,709 | 5/1992 | Aoai et al. . |
| 5,114,832 | 5/1992 | Zertani et al. . |
| 5,124,723 | 6/1992 | Laver . |
| 5,130,227 | 7/1992 | Wade et al. . |
| 5,133,803 | 7/1992 | Moffatt . |
| 5,135,940 | 8/1992 | Belander et al. . |
| 5,139,572 | 8/1992 | Kawashima . |
| 5,139,687 | 8/1992 | Borgher, Sr. et al. . |
| 5,141,556 | 8/1992 | Matrick . |
| 5,141,797 | 8/1992 | Wheeler . |
| 5,144,964 | 9/1992 | Demian . |
| 5,147,901 | 9/1992 | Rutsch et al. . |
| 5,153,104 | 10/1992 | Rossman et al. . |
| 5,153,105 | 10/1992 | Sher et al. . |
| 5,153,166 | 10/1992 | Jain et al. . |
| 5,160,346 | 11/1992 | Fuso et al. . |
| 5,160,372 | 11/1992 | Matrick . |
| 5,166,041 | 11/1992 | Murofushi et al. . |
| 5,169,436 | 12/1992 | Matrick . |
| 5,169,438 | 12/1992 | Matrick . |
| 5,173,112 | 12/1992 | Matrick et al. . |
| 5,176,984 | 1/1993 | Hipps, Sr. et al. . |
| 5,178,420 | 1/1993 | Shelby . |
| 5,180,425 | 1/1993 | Matrick et al. . |
| 5,180,624 | 1/1993 | Kojima et al. . |
| 5,180,652 | 1/1993 | Yamaguchi et al. . |
| 5,181,935 | 1/1993 | Reinert et al. . |
| 5,185,236 | 2/1993 | Shiba et al. . |
| 5,187,045 | 2/1993 | Bonham et al. . |
| 5,187,049 | 2/1993 | Sher et al. . |
| 5,190,565 | 3/1993 | Berenbaum et al. . |
| 5,190,710 | 3/1993 | Kletecka . |
| 5,190,845 | 3/1993 | Hashimoto et al. . |
| 5,193,854 | 3/1993 | Borowski, Jr. et al. . |
| 5,196,295 | 3/1993 | Davis . |
| 5,197,991 | 3/1993 | Rembold . |
| 5,198,330 | 3/1993 | Martic et al. . |
| 5,202,209 | 4/1993 | Winnik et al. . |
| 5,202,210 | 4/1993 | Matsuoka et al. . |
| 5,202,211 | 4/1993 | Vercoulen . |
| 5,202,212 | 4/1993 | Shin et al. . |
| 5,202,213 | 4/1993 | Nakahara et al. . |
| 5,202,215 | 4/1993 | Kanakura et al. . |
| 5,202,221 | 4/1993 | Imai et al. . |
| 5,205,861 | 4/1993 | Matrick . |
| 5,208,136 | 5/1993 | Zanoni et al. . |
| 5,209,814 | 5/1993 | Felten et al. . |
| 5,219,703 | 6/1993 | Bugner et al. . |
| 5,221,334 | 6/1993 | Ma et al. . |
| 5,224,197 | 6/1993 | Zanoni et al. . |
| 5,224,476 | 7/1993 | Schultz et al. . |
| 5,224,987 | 7/1993 | Matrick . |
| 5,226,957 | 7/1993 | Wickramanayake et al. . |
| 5,227,022 | 7/1993 | Leonhardt et al. . |
| 5,230,982 | 7/1993 | Davis et al. . |
| 5,241,059 | 8/1993 | Yoshinaga . |
| 5,244,476 | 9/1993 | Schulz et al. . |
| 5,250,109 | 10/1993 | Chan et al. . |
| 5,254,429 | 10/1993 | Gracia et al. . |
| 5,256,193 | 10/1993 | Winnik et al. . |
| 5,258,274 | 11/1993 | Helland et al. . |
| 5,261,953 | 11/1993 | Vieira et al. . |
| 5,262,276 | 11/1993 | Kawamura . |
| 5,268,027 | 12/1993 | Chan et al. . |
| 5,270,078 | 12/1993 | Walker et al. . |
| 5,271,764 | 12/1993 | Winnik et al. . |
| 5,271,765 | 12/1993 | Ma . |
| 5,272,201 | 12/1993 | Ma et al. . |
| 5,275,646 | 1/1994 | Marshall et al. . |
| 5,279,652 | 1/1994 | Kaufmann et al. . |
| 5,282,894 | 2/1994 | Albert et al. . |
| 5,284,734 | 2/1994 | Blum et al. . |
| 5,286,286 | 2/1994 | Winnik et al. . |
| 5,286,288 | 2/1994 | Tobias et al. . |
| 5,294,528 | 3/1994 | Furutachi . |
| 5,296,275 | 3/1994 | Goman et al. . |
| 5,296,556 | 3/1994 | Frihart . |
| 5,298,030 | 3/1994 | Burdeska et al. . |
| 5,300,403 | 4/1994 | Angelopolus et al. . |
| 5,300,654 | 4/1994 | Nakajima et al. . |
| 5,302,195 | 4/1994 | Helbrecht . |
| 5,302,197 | 4/1994 | Wickramanayke et al. . |
| 5,310,778 | 5/1994 | Shor et al. . |
| 5,312,713 | 5/1994 | Yokoyama et al. . |
| 5,312,721 | 5/1994 | Gesign . |
| 5,324,349 | 6/1994 | Sano et al. . |
| 5,328,504 | 7/1994 | Ohnishi . |
| 5,330,860 | 7/1994 | Grot et al. . |
| 5,334,455 | 8/1994 | Noren et al. . |
| 5,338,319 | 8/1994 | Kaschig et al. . |
| 5,340,631 | 8/1994 | Matsuzawa et al. . |

| | | | | | |
|---|---|---|---|---|---|
| 5,340,854 | 8/1994 | Martic et al. . | 5,747,550 | 5/1998 | Nohr et al. . |
| 5,344,483 | 9/1994 | Hinton . | 5,773,182 | 6/1998 | Nohr et al. . |
| 5,356,464 | 10/1994 | Hickman et al. . | 5,782,963 | 7/1998 | Nohr et al. . |
| 5,362,592 | 11/1994 | Murofushi et al. . | 5,786,132 | 7/1998 | Nohr et al. . |
| 5,368,689 | 11/1994 | Agnemo . | 5,798,015 | 8/1998 | Nohr et al. . |
| 5,372,387 | 12/1994 | Wajda . | 5,811,199 | 9/1998 | MacDonald et al. . |
| 5,372,917 | 12/1994 | Tsuchida et al. . | 5,837,429 | 11/1998 | Nohr et al. . |
| 5,374,335 | 12/1994 | Lindgren et al. . | 5,849,411 | 12/1998 | Nohr et al. . |
| 5,376,503 | 12/1994 | Audett et al. . | 5,855,655 | 1/1999 | Nohr et al. . |
| 5,383,961 | 1/1995 | Bauer et al. . | 5,865,471 | 2/1999 | Nohr et al. . |
| 5,384,186 | 1/1995 | Trinh . | 5,883,161 | 3/1999 | Wood et al. . |
| 5,393,580 | 2/1995 | Ma et al. . | 5,885,337 | 3/1999 | Nohr et al. . |
| 5,401,303 | 3/1995 | Stoffel et al. . | 5,891,229 | 4/1999 | Nohr et al. . |
| 5,401,562 | 3/1995 | Akao . | 5,911,855 | 6/1999 | Dransmann et al. . |
| 5,415,686 | 5/1995 | Kurabayashi et al. . | | | |
| 5,415,976 | 5/1995 | Ali . | | | |

FOREIGN PATENT DOCUMENTS

| | | |
|---|---|---|
| 5,424,407 | 6/1995 | Tanaka et al. . |
| 5,425,978 | 6/1995 | Berneth et al. . |
| 5,426,164 | 6/1995 | Babb et al. . |
| 5,427,415 | 6/1995 | Chang . |
| 5,429,628 | 7/1995 | Trinh et al. . |
| 5,431,720 | 7/1995 | Nagai et al. . |
| 5,432,274 | 7/1995 | Luong et al. . |
| 5,445,651 | 8/1995 | Thoen et al. . |
| 5,445,842 | 8/1995 | Tanaka et al. . |
| 5,455,074 | 10/1995 | Nohr et al. . |
| 5,455,143 | 10/1995 | Ali . |
| 5,459,014 | 10/1995 | Nishijima et al. . |
| 5,464,472 | 11/1995 | Horn et al. . |
| 5,466,283 | 11/1995 | Kondo et al. . |
| 5,474,691 | 12/1995 | Severns . |
| 5,475,080 | 12/1995 | Gruber et al. . |
| 5,476,540 | 12/1995 | Shields et al. . |
| 5,479,949 | 1/1996 | Battard et al. . |
| 5,489,503 | 2/1996 | Toan . |
| 5,498,345 | 3/1996 | Jollenbeck et al. . |
| 5,501,774 | 3/1996 | Burke . |
| 5,501,902 | 3/1996 | Kronzer . |
| 5,503,664 | 4/1996 | Sano et al. . |
| 5,509,957 | 4/1996 | Toan et al. . |
| 5,531,821 | 7/1996 | Wu . |
| 5,532,112 | 7/1996 | Kohler et al. . |
| 5,541,633 | 7/1996 | Winnik et al. . |
| 5,543,459 | 8/1996 | Hartmann et al. . |
| 5,569,529 | 10/1996 | Becker et al. . |
| 5,571,313 | 11/1996 | Mafune et al. . |
| 5,575,891 | 11/1996 | Trokhan et al. . |
| 5,580,369 | 12/1996 | Belding et al. . |
| 5,591,489 | 1/1997 | Dragner et al. . |
| 5,597,405 | 1/1997 | Grigoryan et al. . |
| 5,607,803 | 3/1997 | Murofushi et al. . |
| 5,616,443 | 4/1997 | Nohr et al. . |
| 5,635,297 | 6/1997 | Ogawa et al. . |
| 5,643,356 | 7/1997 | Nohr et al. . |
| 5,643,631 | 7/1997 | Donigian et al. . |
| 5,643,701 | 7/1997 | Nohr et al. . |
| 5,645,964 | 7/1997 | Nohr et al. . |
| 5,672,392 | 9/1997 | De Clercq et al. . |
| 5,681,380 | 10/1997 | Nohr et al. . |
| 5,683,843 | 11/1997 | Nohr et al. . |
| 5,685,754 | 11/1997 | Nohr et al. . |
| 5,686,503 | 11/1997 | Nohr et al. . |
| 5,700,582 | 12/1997 | Sargeant et al. . |
| 5,700,850 | 12/1997 | Nohr et al. . |
| 5,705,247 | 1/1998 | Arai et al. . |
| 5,709,955 | 1/1998 | Nohr et al. . |
| 5,709,976 | 1/1998 | Malhotra . |
| 5,721,287 | 2/1998 | Nohr et al. . |
| 5,733,693 | 3/1998 | Nohr et al. . |
| 5,738,932 | 4/1998 | Kondo et al. . |
| 5,739,175 | 4/1998 | Nohr et al. . |

| | | |
|---|---|---|
| 2437380 | 2/1975 | (DE) . |
| 2444520 | 3/1975 | (DE) . |
| 2416259 | 10/1975 | (DE) . |
| 2714978 | 10/1977 | (DE) . |
| 2722264 | 11/1978 | (DE) . |
| 158237 | 1/1983 | (DE) . |
| 3126433 | 1/1983 | (DE) . |
| 3415033 | 10/1984 | (DE) . |
| 271512 | 9/1989 | (DE) . |
| 3921600 | 1/1990 | (DE) . |
| 3833437 | 4/1990 | (DE) . |
| 3833438 | 4/1990 | (DE) . |
| 004036328 | 7/1991 | (DE) . |
| 4132288 | 4/1992 | (DE) . |
| 4126461 | 2/1993 | (DE) . |
| 0003884 | 9/1979 | (EP) . |
| 0127574 | 12/1984 | (EP) . |
| 0 209 831 | 1/1987 | (EP) . |
| 0223587 | 5/1987 | (EP) . |
| 0262533 | 4/1988 | (EP) . |
| 0280458 | 8/1988 | (EP) . |
| 0 303 803 | 2/1989 | (EP) . |
| 0308274 | 3/1989 | (EP) . |
| 0351615 | 1/1990 | (EP) . |
| 0371304 | 6/1990 | (EP) . |
| 0373662 | 6/1990 | (EP) . |
| 0375160 | 6/1990 | (EP) . |
| 0390439 | 10/1990 | (EP) . |
| 0458140A1 | 10/1991 | (EP) . |
| 0458140 | 11/1991 | (EP) . |
| 0468465 | 1/1992 | (EP) . |
| 0 469 595 | 2/1992 | (EP) . |
| 0 475 075 | 3/1992 | (EP) . |
| 0542286 | 5/1993 | (EP) . |
| 000571190 | 11/1993 | (EP) . |
| 0 605 840 | 7/1994 | (EP) . |
| 0608433 | 8/1994 | (EP) . |
| 0609159 | 8/1994 | (EP) . |
| 0 635 380 | 1/1995 | (EP) . |
| 0639664 | 2/1995 | (EP) . |
| 0 673 779 | 9/1995 | (EP) . |
| 0 716 929 | 6/1996 | (EP) . |
| 0 737 592 | 10/1996 | (EP) . |
| 0755984 | 1/1997 | (EP) . |
| 0 805 152 | 11/1997 | (EP) . |
| 0 861 880 | 9/1998 | (EP) . |
| 2245010 | 4/1975 | (FR) . |
| 2383157 | 10/1978 | (FR) . |
| 275245 | 10/1928 | (GB) . |
| 349339 | 5/1931 | (GB) . |
| 355686 | 8/1931 | (GB) . |
| 399753 | 10/1933 | (GB) . |
| 441085 | 1/1936 | (GB) . |
| 779389 | 7/1957 | (GB) . |
| 1150987 | 5/1969 | (GB) . |

| | | | | | | |
|---|---|---|---|---|---|---|
| 1372884 | 11/1974 | (GB) . | | 89014948 | 3/1989 | (JP) . |
| 2146357 | 4/1985 | (GB) . | | 1-128063 | 5/1989 | (JP) . |
| 662500 | 4/1964 | (IT) . | | 1146974 | 6/1989 | (JP) . |
| 424756 | 6/1934 | (JP) . | | 01210477 | 8/1989 | (JP) . |
| 43-15663 | 7/1968 | (JP) . | | 1288854 | 11/1989 | (JP) . |
| 47-26653 | 7/1972 | (JP) . | | 2-58573 | 2/1990 | (JP) . |
| 47-45409 | 11/1972 | (JP) . | | 292957 | 4/1990 | (JP) . |
| 49-8909 | 2/1974 | (JP) . | | 2179642 | 7/1990 | (JP) . |
| 50-65592 | 6/1975 | (JP) . | | 2282261 | 11/1990 | (JP) . |
| 51-17802 | 2/1976 | (JP) . | | 3-134072 | 6/1991 | (JP) . |
| 53-104321 | 9/1978 | (JP) . | | 03163566 | 7/1991 | (JP) . |
| 55-62059 | 5/1980 | (JP) . | | 3-170415 | 7/1991 | (JP) . |
| 55-90506 | 7/1980 | (JP) . | | 3-206439 | 9/1991 | (JP) . |
| 56-8134 | 1/1981 | (JP) . | | 3-258867 | 11/1991 | (JP) . |
| 0014233 | 2/1981 | (JP) . | | 3-203694 | 12/1991 | (JP) . |
| 56-14569 | 2/1981 | (JP) . | | 3284668 | 12/1991 | (JP) . |
| 56-24472 | 3/1981 | (JP) . | | 4023884 | 1/1992 | (JP) . |
| 56-36556 | 4/1981 | (JP) . | | 4023885 | 1/1992 | (JP) . |
| 0029284 | 5/1981 | (JP) . | | 4-45174 | 2/1992 | (JP) . |
| 57-61055 | 4/1982 | (JP) . | | 4100801 | 4/1992 | (JP) . |
| 57-128283 | 8/1982 | (JP) . | | 4-136075 | 5/1992 | (JP) . |
| 57-171775 | 10/1982 | (JP) . | | 04356087 | 12/1992 | (JP) . |
| 58-124452 | 7/1983 | (JP) . | | 543806 | 2/1993 | (JP) . |
| 58-125770 | 7/1983 | (JP) . | | 561220 | 3/1993 | (JP) . |
| 58-222164 | 12/1983 | (JP) . | | 5080506 | 4/1993 | (JP) . |
| 59-89360 | 5/1984 | (JP) . | | 05119506 | 5/1993 | (JP) . |
| 29219270 | 12/1984 | (JP) . | | 5134447 | 5/1993 | (JP) . |
| 59-219270 | 4/1985 | (JP) . | | 5-140498 | 6/1993 | (JP) . |
| 60-192729 | 10/1985 | (JP) . | | 2-219869 | 9/1993 | (JP) . |
| 60-239739 | 11/1985 | (JP) . | | 5263067 | 10/1993 | (JP) . |
| 60-239740 | 11/1985 | (JP) . | | 680915 | 3/1994 | (JP) . |
| 60-239741 | 11/1985 | (JP) . | | 6116555 | 4/1994 | (JP) . |
| 60-239743 | 11/1985 | (JP) . | | 6116556 | 4/1994 | (JP) . |
| 61-14994 | 1/1986 | (JP) . | | 6116557 | 4/1994 | (JP) . |
| 61-14995 | 1/1986 | (JP) . | | 6-175584 | 6/1994 | (JP) . |
| 61-21184 | 1/1986 | (JP) . | | 6214339 | 8/1994 | (JP) . |
| 61-288 | 1/1986 | (JP) . | | 6256494 | 9/1994 | (JP) . |
| 61-3781 | 1/1986 | (JP) . | | 6256633 | 9/1994 | (JP) . |
| 61-25885 | 2/1986 | (JP) . | | 7113828 | 4/1972 | (NL) . |
| 61-30592 | 2/1986 | (JP) . | | 1310767 | 5/1987 | (RU) . |
| 61-40366 | 2/1986 | (JP) . | | 1772118 | 10/1992 | (SU) . |
| 61-77846 | 4/1986 | (JP) . | | 92/11295 | 7/1992 | (WO) . |
| 61-128973 | 6/1986 | (JP) . | | 93/06597 | 4/1993 | (WO) . |
| 61-97025 | 9/1986 | (JP) . | | 94/01503 | 1/1994 | (WO) . |
| 61-222789 | 10/1986 | (JP) . | | 94/22500 | 10/1994 | (WO) . |
| 61-247703 | 11/1986 | (JP) . | | 94/22501 | 10/1994 | (WO) . |
| 62-285403 | 12/1986 | (JP) . | | 95/04955 | 2/1995 | (WO) . |
| 62-7703 | 1/1987 | (JP) . | | 95/28285 | 10/1995 | (WO) . |
| 62-100557 | 5/1987 | (JP) . | | 96/00740 | 1/1996 | (WO) . |
| 62-97881 | 5/1987 | (JP) . | | 96/19502 | 6/1996 | (WO) . |
| 62-127281 | 6/1987 | (JP) . | | 96/22335 | 7/1996 | (WO) . |
| 63-43959 | 2/1988 | (JP) . | | 96/24636 | 8/1996 | (WO) . |
| 63-48370 | 3/1988 | (JP) . | | 97/20000 | 6/1997 | (WO) . |
| 63-95439 | 4/1988 | (JP) . | | 97/35933 | 10/1997 | (WO) . |
| 63-95440 | 4/1988 | (JP) . | | 98/23695 | 6/1998 | (WO) . |
| 63-95445 | 4/1988 | (JP) . | | | | |
| 63-95446 | 4/1988 | (JP) . | | | | |
| 63-95447 | 4/1988 | (JP) . | | | | |
| 63-95448 | 4/1988 | (JP) . | | | | |
| 63-95449 | 4/1988 | (JP) . | | | | |
| 63-95450 | 4/1988 | (JP) . | | | | |
| 63-151946 | 6/1988 | (JP) . | | | | |
| 63-164953 | 7/1988 | (JP) . | | | | |
| 63-165498 | 7/1988 | (JP) . | | | | |
| 63-223077 | 9/1988 | (JP) . | | | | |
| 63-223078 | 9/1988 | (JP) . | | | | |
| 63-243101 | 10/1988 | (JP) . | | | | |
| 63-199781 | 12/1988 | (JP) . | | | | |
| 64-15049 | 1/1989 | (JP) . | | | | |
| 6429337 | 1/1989 | (JP) . | | | | |
| 64-40948 | 2/1989 | (JP) . | | | | |

OTHER PUBLICATIONS

Wijesekera, T.P., et al., Synthetic Aspects of Pophyrin and Metalloporphyrin Chemistry, *Metalloporpyrins in Catalytic Oxidations*, pp. 202–203, 206–207, 1994.

Derwent Publications Ltd., London, JP 05297627(Fujitsu Ltd.), Nov. 12, 1993. (Abstract), 1993.

Patent Abstracts of Japan, JP 5241369 (Bando Chem Ind Ltd et al.), Sep. 21, 1993. (Abstract), 1993.

Derwent Publications Ltd., London, JP 05232738 (Yamazaki, T.). Sep. 10, 1993. (Abstract), 1993.

Derwent Publications Ltd., London, EP 000559310 (Zeneca Ltd.), Sep. 8, 1993. (Abstract), 1993.

Derwent Publications Ltd., London, J,A, 5–230410 (Seiko Epson Corp), Sep. 7, 1993. (Abstract), 1993.
Derwent Publications Ltd., London, JP 5–230407 (Mitsubishi Kasei Corp), Sep. 7, 1993. (Abstract), 1993.
Abstract Of Patent, JP 405230410 (Seiko Epson Corp.), Sep. 7, 1993. (Abstract), 1993.
Abstract Of Patent, JP 405230407 (Mitsubishi Kasei Corp.), Sep. 7, 1993. (Abstract), 1993.
Patent Abstracts of Japan, JP 5197198 (Bando Chem Ind Ltd et al.), Aug. 6, 1993. (Abstract), 1993.
Database WPI—Derwent Publications Ltd., London, J,A, 5197069 (Bando Chem), Aug. 6, 1993. (Abstract), 1993.
Abstract of patent, JP 5–195450 (Nitto Boseki Co. Ltd), Aug. 3, 1993. 1993.
Derwent World Patents Index, JP 5186725 (Seiko Epson Corp.), Jul. 27, 1993. abstract, 1993.
Patent Abstracts of Japan, JP 5181308 (Bando Chem Ind Ltd et al.), Jul. 23, 1993. (Abstract), 1993.
Patent Abstracts of Japan, JP 5181310 (Bando Chem Ind Ltd et al.), Jul. 23, 1993. (Abstract), 1993.
Derwent Publications Ltd., London, JP 5–132638 (Mitsubishi Kasei Corp), May 28, 1993. (Abstract), 1993.
Abstract Of Patent, JP 405132638 (Mitsubishi Kasei Corp.), May 28, 1993. (Abstract), 1993.
Derwent Publications Ltd., London, JP 5–125318 (Mitsubishi Kasei Corp), May 21, 1993. (Abstract), 1993.
Abstract Of Patent, JP 405125318 (Mitsubishi Kasei Corp.), May 21, 1993. (Abstract), 1993.
Abstract of patent, JP 05–117200 (Hidefumi Hirai et al.) (May 14, 1993), 1993.
Derwent World Patents Index. JP 5117105 (Mitsui Toatsu Chem Inc.) May 14, 1993. 1993.
Derwent Publications Ltd., London, JP 05061246 (Ricoh KK), Mar. 12, 1993. (Abstract), 1993.
Husain, N. et al., "Cyclodextrins as mobile–phase additives in reversed–phase HPLC", *American Laboratory*, 82, 80–87, 1993.
Hamilton, D.P., "Tired of Shredding? New Ricoh Method Tries Different Tack", *Wall Street Journal*, B2, 1993.
"Cyclodextrins: A Breakthrough for Molecular Encapsulation", *American Maize Products Co. (AMAIZO)*, 1993.
Duxbury, "The Photochemistry and Photophysics of Triphenylmethane Dyes in Solid Liquid Media", *Chemical Review*, 93, 381–433, 1993.
Abstract of patent, JP 04–351603 (Dec. 7, 1992), 1992.
Abstract of patent, JP 04–351602, 1992.
Derwent Publications Ltd., London, JP 404314769 (Citizen Watch Co. Ltd.), Nov. 5, 1992. (Abstract), 1992.
Abstract of patent, JP 04315739, 1992.
Derwent Publications Ltd., London, JP 04300395 (Funai Denki KK), Oct. 23, 1992. (Abstract), 1992.
Derwent Publications Ltd., London, JP 404213374 (Mitsubishi Kasei Corp), Aug. 4, 1992. (Abstract), 1992.
Abstract of patent, JP 04–210228, 1992.
Abstract Of Patent, JP 404202571 (Canon Inc.), Jul. 23, 1992. (Abstract), 1992.
Abstract Of Patent, JP 404202271 (Mitsubishi Kasei Corp.), Jul. 23, 1992. (Abstract), 1992.
Derwent WPI, JP 4–197657 (Toshiba KK) Jul. 17, 1992, abstract. 1992.
Derwent Publications Ltd., London, JP 4–189877 (Seiko Epson Corp), Jul. 8, 1992. (Abstract), 1992.
Derwent Publications Ltd., London, JP 404189876 (Seiko Epson Corp), Jul. 8, 1992. (Abstract), 1992.
Abstract Of Patent, JP 404189877 (Seiko Epson Corp.). Jul. 8, 1992. (Abstract), 1992.
Derwent Publications Ltd., London, J,A, 4–170479 (Seiko Epson Corp), Jun. 18, 1992. (Abstract), 1992.
Abstract of patent, JP 04–81402, 1992.
Abstract of patent, JP 04–81401, 1992.
Kogelschatz, "Silent–discharge driven excimer UV sources and their applications", *Applied Surface Science*, 410–423, 1992.
Derwent Publications, Ltd., London, JP 403269167 (Japan Wool Textile KK). Nov. 29, 1991 (Abstract), 1991.
Derwent Publications Ltd., London, JO 3247676 (Canon KK), Nov. 5, 1991 (Abstract), 1991.
Abstract of patent, JP 03–220384, 1991.
Patent Abstracts of Japan, JP 03184896 (Dainippon Printing Co Ltd.) Aug. 12, 1991. 1991.
Derwent Publications Ltd., London, JP 3167270 (Mitsubishi Kasei Corp), Jul. 19, 1991. (Abstract), 1991.
Derwent Publications Ltd., London, JO 3167270 (Mitsubishi Kasei Corp.), Jul. 19, 1991 (Abstract), 1991.
Derwent World Patents Index, EP 435536 (Canon KK) Jul. 3, 1991. abstract, 1991.
Derwent Publications Ltd., London, JO 3093870 (Dainippon Ink Chem KK.), Apr. 18, 1991 (Abstract), 1991.
Abstract of patent, JP 06369890, 1991.
Kogelschatz, U. et al., "New Excimer UV Sources for Industrial Applications", *ABB Review*, 391, 1–10, 1991.
Abstract of patent, JP 03–41165, 1991.
"Coloring/Decoloring Agent for Tonor Use Developed", *Japan Chemical Week*, 1991.
Braithwaite, M., et al., "Formulation", *Chemistry & Technology of UV & EB Formulation for Coatings, Inks & Paints*, IV, 11–12, 1991.
*Scientific Polymer Products, Inc. Brochure*, 24–31, 1991.
Dietliker, K., "Photoiniators for Free Radical and Catioinc Polymerisation", *Chem & Tech of UV & EB Formulation for Coatings, Inks & Paints*, III, 61, 63, 229–232, 280, 405, 1991.
Esrom et al., "Large area Photochemical Dry Etching of Polymers iwth Incoherent Excimer UV Radiation", *MRS Materials Research Society*, 1–7, 1991.
Esrom et al., Excimer Laser–Induced Decompostion of Aluminum Nitride, *Materials Research Society Fall Meeting*, 1–6, 1991.
Esrom et al., "Metal deposition with a windowless VUV excimer source", *Applied Surface Science*, 1–5, 1991.
Esrom, "Excimer Laser–Induced Surface Activation of Aln for Electroless Metal Deposition", *Mat. Res. Sco.lSymp. Proc.*, 204, 457–465, 1991.
Zhang et al., "UV–induced decompositin of adsorbed Cu–acetylacetonate films at room temperature for electroless metal plating", *Applied Surface Science*, 1–6, 1991.
"German company develops reuseable paper", *Pulp & Paper*, 1991.
Abstract of patent, JP 02289652, 1990.
Ohashi et al., "Molecular Mechanics Studies on Inclusion Compounds of Cyanine Dye Monomers and Dimers in Cyclodextrin Cavities," *J. Am. Chem. Soc.*, 112, 5824–5830, 1990.
Kogelschatz et al., "New Incoherent Ultraviolet Excimer Sources for Photolytic Material Deposition," *Laser Und Optoelektronik*, 1990.
Patent Abstracts of Japan, JP 02141287 (Dainippon Printing Co Ltd.) May 30, 1990. 1990.

Abstract of Patent, JP 0297957, (Fuji Xerox Co., Ltd.), 1990.
Derwent Publications Ltd., London, JP 2091166 (Canon KK), Mar. 30, 1990. (Abstract), 1990.
Esrom et al., "Metal Deposition with Incoherent Excimer Radiation", *Mat. Res. Soc. Symp. Proc.*, 158, 189–198, 1990.
Esrom, "UV Excimer Laser–Induced Deposition of Palladium from palladiym Acetate Films", *Mat. Res. Soc. Symp. Proc.*, 158, 109–117, 1990.
Kogelschatz, U., "Silent Discharges for the Generation of ultraviolet and vacuum ultraviolet excimer radiation", *Pure & Applied Chem.*, 62, 1667–74, 1990.
Esrom et al., "Investigation of the mechanism of the UV–induced palladium depostions processf from thin solid palladium acetate films", *Applied Surface Science*, 46, 158–162, 1990.
Zhang et al., "VUV synchrotron radiation processing of thin palladium acetate spin–on films for metallic surface patterning", *Applied Surface Science*, 46, 153–157, 1990.
Brennan et al., "Stereoelectronic effects in ring closure reactions: the 2'–hydroxychalcone—flavanone equilibrium, and related systems,", *Canadian J. Chem.*, 68 (10), pp. 1780–1785, 1990.
Abstract of patent, JP 01–299083, 1989.
Derwent Publications Ltd., London, J,0, 1182379 (Canon KK), Jul. 20, 1989. (Abstract), 1989.
Derwent Publications Ltd., London, JO 1011171 (Mitsubishi Chem Ind. KK.), Jan. 13, 1989 (Abstract), 1989.
Gruber, R.J., et al., "Xerographic Materials", *Encyclopedia of Polymer Science and Engineering*, 17, 918–943, 1989.
Pappas, S.P., "Photocrosslinking", *Comph. Pol. Sci.*, 6, 135–148, 1989.
Pappas, S.P., "Photoinitiated Polymerization", *Comph. Pol. Sci.*, 4, 337–355, 1989.
Kirilenko, G.V. et al., "An analog of the vesicular process with amplitude modulation of the incident light beam", *Chemical Abstracts*, 111, 569 [No. 111:123633b], 1989.
Esrom et al., "UV excimer laser–induced pre–nucleation of surfaces followed by electroless metallization", *Chemtronics*, 4, 216–223, 1989.
Esrom et al., "VUV light–induced depostion of palladium using an incoherent Xe2* excimer source", *Chemtronics*, 4, 1989.
Esrom et al., "UV Light–Induced Depostion of Copper Films", C5–719–C5–725, 1989.
Falbe et al., *Rompp Chemie Lexikon*, 9, 270, 1989.
Allen, Norman S., *Photopolymerisation and Photoimaging Science and Technology*, pp. 188–199; 210–239, 1989.
Patent Abstracts of Japan, JP 63297477 (Fuji Photo Film Co. Ltd.) Dec. 5, 1988, abstract. 1988.
Derwent Publications, Ltd., London, SU 1423656 (Kherson Ind Inst), Sep. 15, 1988 (Abstract), 1988.
Derwent Publications, Ltd., London, EP 0280653 (Ciba Geigy AG), Aug. 31, 1988 (Abstract), 1988.
Abstract of patent, JP 63–190815, 1988.
Patent Abstracts of Japan, JP 63179985 (Tomoegawa Paper Co. Ltd.), Jul. 23, 1988, 1988.
Derwent World Patents Index, JP 63179977 (Tomoegawa Paper Mfg Co Ltd), Jul. 23, 1988, 1988.
Furcone, S.Y. et al., "Spin–on Bl4Sr3Ca3Cu4O16+x super-conducting thin films from citrate precursors," *Appl. Phys. Lett.*, 52(25), 2180–2182, 1988.
Abstract of patent, JP 63–144329, 1988.
Abstract of patent, JP 63–130164, 1988.

Derwent Publications, Ltd., London, J6 3112770 (Toray Ind Inc), May 17, 1988 (Abstract), 1988.
Derwent Publications, Ltd., London, J6 3108074 (Konishiroku Photo KK), May 12, 1988 (Abstract), 1988.
Derwent Publications, Ltd., London,J6 3108073 (Konishiroku Photo KK), May 12, 1988 (Abstract), 1988.
Abstract of patent, JP 61–77846, 1988.
Abstract of patent, JP 63–73241, 1988.
Abstract of patent, JP 63–47762, 1988.
Abstract of patent, JP 63–47763, 1988.
Abstract of patent, JP 63–47764, 1988.
Abstract of patent, JP 63–47765, 1988.
Eliasson, B., et al., "UV Excimer Radiation from Dielectric–Barrier Discharges", *Applied Physics B*, 46, 299–303, 1988.
Eliasson et al., "New Trends in High Intensity UV Generation", *EPA Newsletter*, (32), 29–40, 1988.
Cotton, F.A., "Oxygen: Group Via(16)", *Advanced Inorganic Chemistry*, 5th ed., 473–474, 1988.
Derwent Publications, Ltd., London, J6 2270665 (Konishiroku Photo KK), Nov. 25, 1987, (Abstract), 1987.
Abstract of patent, JP 62–215261, 1987.
Derwent World Patents Index, JP 62064874 (Dainichiseika Color & Chem Mfg.), Mar. 23, 1987. abstract, 1987.
Database WPI, Derwent Publications Ltd., London, JP 62032082 (Mitsubishi Denki KK), Feb. 12, 1987. (Abstract), 1987.
Abstract of patent, JP 62–32082, 1987.
Derwent Publications Ltd., London, J6 2007772 (Alps Electric KK.), Jan. 14, 1987 (Abstract), 1987.
Gross et al., "Laser direct–write metallization in thin palladium acetate films", *J. App. Phys.*, 61(4), 1628–1632, 1987.
Al–Ismail et al., "Some experimental results on thin polypropylene films loaded with finely–dispersed copper", *Journal of Materials Science*, 415–418, 1987.
Baufay et al., "Optical self–regulation during laser–induced oxidation of copper", *J. Appl. Phys*, 61(9), 4640–4651, 1987.
Derwent Publications Ltd., London, JA 0284478 (Sanyo Chem Ind Ltd.), Dec. 15, 1986 (Abstract), 1986.
Abstract of patent, JP 61251842, 1986.
Database WPI, Derwent Publications Ltd., London, GB; SU, A, 1098210 (Kutulya L A) Jun. 23, 1986. 1986.
Abstract of patent, JP 61–97025, 1986.
Abstract of patent, JP 61–87760, 1986.
Derwent Publications Ltd., London, DL 0234731 (Karl Marx Univ. Leipzig), Apr. 9, 1986. (Abstract), 1986.
Derwent World Patents Index, SU 1219612 (AS USSR NON–AQ SOLN) Mar. 23, 1986. 1986.
Derwent Publications, Ltd., London, J6 1041381 (Osaka Prefecture), Feb. 27, 1986 (Abstract), 1986.
Dialog, JAPIO, JP 61–034057 (Ciba Geigy AG) Feb. 18, 1986. 1986.
Derwent World Patents Index, JP 61027288 (sumimoto Chem Ind KK) Feb. 6, 1986. 1986.
Sakai et al., "A Novel and Practical Synthetic Method of 3(2H)–Furanone Derivatives," *J. Heterocyclie Chem.*, 23, pp. 1199–1201, 1986.
Jellinek, H.H.G. et al., "Evolution of H2O and CO2 During the Copper–Catalyzed Oxidation of Isotactic Polypropylene," *J. Polymer Sci.*, 24, 389–403, 1986.

Jellinek, H.H.G. et al., "Diffusion of Ca2+ Catalysts from Cu–Metal Polymer or Cu–Oxide/Polymer Interfaces into Isotactic Polypropylene," *J. Polymer Sci.*, 24, 503–510, 1986.

John J. Eisch and Ramiro Sanchez, "Selective, Oxophilic Imination of Ketones with Bis (dichloroaluminum) Phenylimide", *J. Org. Chem.*, 51 (10), 1848–1852, 1986.

Derwent Publications Ltd., London, J6 0226575 (Sumitomo Chem Ind Ltd.), Oct. 11, 1985 (Abstract), 1985.

Abstract of patent, JP 60–156761, 1985.

Derwent World Patents Index, DE 3443565 (Mitsubishi Yuka Fine Che. et al.) Jul. 11, 1985. abstract, 1985.

Derwent Publications Ltd., London, J,A, 0011451 (Fugi Photo Film KK), Jan. 21, 1985. (Abstract), 1985.

Derwent Publications, Ltd., London J6 0011449–A (Taoka Chemical KK) Jan. 21, 1985 (abstract), 1985.

Derwent World Patents Index, JP 60–008088 (Mitsubishi Paper Mills Ltd.) Jan. 16, 1985. abstract, 1985.

Roos, G. et al., "Textile applications of photocrosslinkable polymers", *Chemical Abstracts*, 103, 57 [No. 103:23690j], 1985.

Beck, M.T., et al., Mechanism of the autophotosensitized formulation of porphyrins in the reaction of pyrrole and m–disulfonated, *Chemical Abstracts*, 1985:45362, 1985.

Derwent World Patents Index, EP 127574 (Ciba Geigy AG), Dec. 5, 1984, 1984.

Derwent Publications Ltd., London, JP 0198187 (Canon KK), Nov. 9, 1984. (Abstract), 1984.

Derwent Publications Ltd., Londn, J,A, 0169883 (Ricoh KK), Sep. 25, 1984. (Abstract), 1984.

Derwent Publications Ltd., London, JA 0198187 (Canon KK), Nov. 9, 1984 (Abstract), 1984.

Derwent Publications Ltd., London, J,A, 0053563 (Dainippon Toryo KK), Mar. 28, 1984. (Abstract), 1984.

Derwent Publications Ltd., London, J,A, 0053562 (Dainippon Toryo KK), Mar. 28, 1984. (Abstract), 1984.

Abstract of Patent, JA 0053563 (Dainippon Toryo KK), Mar. 28, 1984 (Abstract), 1984.

Abstract of Patent, JA 0053562 (Dainippon Toryo KK), Mar. 28, 1984 (Abstract), 1984.

Derwent Publications Ltd., London, J,A, 0051961 (Dainippon Toryo KK), Mar. 26, 1984). (Abstract), 1984.

Abstract of Patent, JA 0051961 (Dainippon Toryo KK), Mar. 26, 1984 (Abstract), 1984.

Saenger, W., "Structural Aspects of Cyclodextrins and Their Inclusion Complexes", *Inclusion Compounds—Structural Aspects of Inclusion Compounds formed by Organic Host*, 2, 231–259, 1984.

Szejtli, "Industrial Applications of Cyclodextrins", *Inclusion Compounds: Physical Prop. & Applns*, 3, 331–390, 1984.

Kano et al., "Three–Component Complexes of Cyclodextrins. Exciplex Formation in Cyclodextrin Cavity," *J. Inclusion Phenomena* 2, pp. 737–746, 1984.

Suzuki et al., "Spectroscopic Investigation of Cyclodextrin Monomers, Derivatives, Polymers and Azo Dyes." *J. Inclusion Phenomena* 2, pp. 715–724, 1984.

Abstract of Patent, JA 0222164 (Ricoh KK), Dec. 23, 1983 (Abstract), 1983.

Abstract of patent, JP 58211426 (Sekisui Plastics KK), (Dec. 8, 1983), 1983.

Derwent Publications, Ltd., London, EP 0072775 (Ciba Geigy AG), Feb. 23, 1983 (Abstract), 1983.

van Beek, H.C.A, "Light–Induced Colour Changes in Dyes and Materials", *Color Res. and Appl.*, 8, 176–181, 1983.

Connors, K.A., "Application of a stoichiometric model of cyclodextrin complex formation", *Chemical Abstracts*, 98, 598 [No. 98:53067g], 1983.

Abstract of Patent, EP 0065617 (IBM Corp.), Dec. 1, 1982 (Abstract), 1982.

Derwent Publications Ltd., London, J,A, 0187289 (Honshu Paper Mfg KK), Nov. 17, 1982. (Abstract), 1982.

Abstract of Patent, JA 0187289 (Honsho Paper Mfg KK), Nov. 17, 1982 (Abstract), 1982.

Abstract of Patent, JA 0185364 (Ricoh KK), Nov. 15, 1982 (Abstract), 1982.

Derwent Publications, Ltd., London J5 7139146 (Showa Kako KK) Aug. 27, 1982 (abstract), 1982.

Abstract of Patent, JA 0090069 (Canon KK), Jun. 4, 1982 (Abstract), 1982.

Derwent Publications, Ltd., London, JA 0061785 (Nippon Senka KK), Apr. 14, 1982 (Abstract), 1982.

Fischer, "Submicroscopic contact imaging with visible light by energy transfer", *Appl. Phys. Letter*, 40(3), 1982.

Abstract of Patent, JA 0010659 (Canon KK), Jan. 20, 1982 (Abstract), 1982.

Abstract of Patent, JA 0010661 (Canon KK), Jan. 20, 1982 (Abstract), 1982.

Christen, "Carbonylverbindungen: Aldehyde und Ketone," *Grundlagen der Organischen Chemie*, 255, 1982.

Derwent Publications Ltd., London. J,A, 0155263 (Canon KK), Dec. 1, 1981. (Abstract), 1981.

Abstract of Patent, JA 0155263 (Canon KK), Dec. 1, 1981 (Abstract), 1981.

Abstract of Patent, JA 0147861 (Canon KK), Nov. 17, 1981 (Abstract), 1981.

Derwent Publications Ltd., London, J,A, 0143273 (Canon KK), Nov. 7, 1981. (Abstract), 1981.

Abstract of Patent, JP 56143272 (Canon KK), Nov. 7, 1981 (Abstract), 1981.

Patent Abstracts of Japan, JP 56143274 (Canon Inc.) Nov. 7, 1981, abstract. 1981.

Abstract of Patent, JA 0136861 (Canon KK), Oct. 26, 1981 (Abstract), 1981.

Abstract of Patent, JA 6133378 (Canon KK), Oct. 19, 1981 (Abstract), 1981.

Abstract of Patent, JA 6133377 (Canon KK), Oct. 19, 1981 (Abstract), 1981.

Abstract of Patent, JA 6093775 (Canon KK), Jul. 29, 1981 (Abstract), 1981.

Derwent Publications Ltd., London, J,A, 0008135 (Ricoh KK), Jan. 27, 1981. (Abstract), 1981.

Derwent Publications Ltd., London, J,A, 0004488 (Canon KK), Jan. 17, 1981. (Abstract), 1981.

Abstract of Patent, JA 0004488 (Canon KK), Jan. 17, 1981 (Abstract), 1981.

Kirk–Othmer, "Metallic Coatings," *Encyclopedia of Chemical Technology*, 15, 241–274, 1981.

Komiyama et al., "One–Pot Preparation of 4–Hydroxychalcone β–Cyclodextrin as Catalyst," *Makromol. Chem.*, 2, 733–734, 1981.

Derwent Publications, Ltd., London CA 1086–719 (Sherwood Medical) Sep. 30, 1980 (abstract), 1980.

Derwent Publications Ltd., Database WPI, JP 55 113036 (Ricoh KK), Sep. 1, 1980, 1980.

Rosanske et al., "Stoichiometric Model of Cyclodextrin Complex Formation", *Journal of Pharmaceutical Sciences*, 69(5), 564–567, 1980.

Semple et al., "Synthesis of Functionalized Tetrahydrofurans," *Tetrahedron Letters*, 81, pp. 4561–4564, 1980.

Kirk–Othmer, "Film Deposition Techniques," *Encyclopedia of Chemical Technology*, 10, 247–283, 1980.

Derwent World Patents Index, Derwent Info. Ltd., JP 54158941 (Toyo Pulp KK), Dec. 15, 1979. (Abstract), 1979.

Derwent World Patents Index, JP 54117536 (Kawashima F) Sep. 12, 1979. 1979.

Derwent Publications Ltd., London, J,A, 0005422 (Fuji Photo Film KK), Jan. 16, 1979. (Abstract), 1979.

Drexhage et al., "Photo–bleachable dyes and processes", *Research Disclosure*, 85–87, 1979.

"Color imaging devices and color filter arrays using photo–bleachable dyes", *Research Disclosure*, 22–23, 1979.

Wolff, N.E., et al., "Electrophotography", *Kirk–Othmer Encyclopedia of Chemical Technology*, 8, 794–826, 1979.

Derwent Publications Ltd., London, J,A, 0012037 (Pentel KK), Jan. 29, 1977. (Abstract), 1977.

Abstract of Patent, JA 0012037 (Pentel KK), Jan. 29, 1977 (Abstract), 1977.

Jenkins, P.W. et al., "Photobleachable dye material", *Research Disclosure*, 18 [No. 12932], 1975.

Lamberts, R.L., "Recording color grid pattens with lenticules", *Research Disclosure*, 18–19 [No. 12923], 1975.

Karmanova, L.S. et al., "Light stabilizers of daytime fluorescent paints", *Chemical Abstracts*, 82, 147 [No. 59971p], 1975.

Prokopovich, B. et al., "Selection of effective photoinducers for rapid hardening of polyester varnish PE–250", *Chemical Abstracts*, 83, 131 [No. 81334a], 1975.

"Variable Contrast Printing System", *Research Disclosure*, 19 [No. 12931], 1975.

Lakshman, "Electronic Absorption Spectrum of Copper Formate Tetrahydrate", *Chemical Physics Letters*, 31(2), 331–334, 1975.

Derwent Publications, Ltd., London J4 9131–226 (TNational Cash Register C) Dec. 16, 1974 (abstract), 1974.

Chang, I.F., et al., "Color Modulated Dye Ink Jet Printer", *IBM Technical Disclosure Bulletin*, 17(5), 1520–1521, 1974.

"Darocur 1173: Liquid Photoiniator for Ultraviolet Curing of Coatings", 1974.

Hosokawa et al., "Ascofuranone, an antibiotic from Ascochyta," Japan Kokai 73 91,278 (Nov. 28, 1973), *Merck Index*, 80, p. 283; abstract 94259t, 1974.

Abstract of patent. NL 7112489 (Dec. 27, 1971). 1971.

Gafney et al., "Photochemical Reactions of Copper (II)—1,3–Diketonate Complexes", *Journal of the Americqal Chemical Society*, 1971.

Derwent Publications, Ltd., London SU 292698–S (Jan. 15, 1971 (abstract), 1971.

Derwent World Patents Index,CS 120380 (Kocourek, Jan) Oct. 15, 1966. 1966.

Tsuda, K., et al., Vinyl Polymerization. CXLVI. The influence of dibenzoyl disulfide derivatives on radical polymerizations, *Chemical Abstract*, 1966:29198, 1966.

Rigdon, J.E., "In Search of Paper that Spies Can't Copy", *Wall Street Journal*.

Chatterjee,S. et al., "Photochemistry of Carbocyanine Alkyltriphenylborate Salts: Intra–Ion–Pair Electron Transfer and the Chemistry of Boranyl Radicals", *J. Am. Chem. Soc.*, 112, 6329–6338.

"Assay—Physical and Chemical Analysis of Complexes", *AMAIZO*.

"Cyclodextrin", *AMAIZO*.

"Beta Cyclodextrin Polymer (BCDP)", *AMAIZO*.

"Chemically Modified Cyclodextrins", *AMAIZO*.

"Cyclodextrin Complexation", *American Maize Products Co.*.

"Monomers", *Scientific Polymer Products Inc.*.

Suppan, Paul, "Quanching of Excited States", *Chemistry and Light*, 65–69.

Tamaguchi, H. et al., "Supersensitization. Aromatic ketones as supersensitizers", *Chemical Abstracts*, 53, 107 (d).

Stecher, H., "Ultraviolet–absorptive additives in adhesives, lacquers and plastics", *Chemical Abstracts*, 53, 14579 (c).

Maslennikov, A.S., "Coupling of diazonium salts with ketones", *Chemical Abstracts*, 60, 3128e.

Derwent Publications Ltd., London, 4 9128022.

Abstract of Patent, JP 405195450.

Rose, Philip I., "Gelatin," *Encyclopedia of Chemical Technology*, 7, 488–513.

Tsuda et al. Decomposition, initiation, and chain transfer of dibenzoyldisulfane. Makromol. Chem, 2111–2120, 175(5), 1974.

Aroba, Kanwar et al. Photoreactions of beta–keto sulfides: aryl and phenacyl sulfides and related compounds. J. Chem. REs., Synop, 184–185, 6 1985.

Beelitz, Klaus. Organic Photochemistry. 22. Organic sulfur componds . 30. Photochemical alpha splitting of mixed thioanhydrides substituted thiobenzoic acids with O–ethylxanthgenic acid. Chem. –Ztg, 67, 102 (2) 1978.

Sato et al. Applicantion of spin trapping techniques to radical polymerization, 15. Photo–decomposition of dibenzoyl disulfide and evaluation of relative reactivities of vinyl monomers towards benzoyl radicals. Makrmol. Chem., 1951–1958, 178(7), 1997.

Otsu, Takayuki et al. ROle of initiator–transfer agent–terminator radical polymerizations: Polymer desin by organic disulfides as iniferters. Makromol. Chem., Rapid Commun. 127–132, 3(2) 1982.

* cited by examiner

PHOTOINITIATORS AND APPLICATIONS THEREFOR

TECHNICAL FIELD

The present invention relates to a novel photoinitiators and methods for generating a reactive species using the photoinitiators. The present invention, further relates to methods of polymerizing or photocuring polymerizable unsaturated material using the above-mentioned photoinitiators.

BACKGROUND OF THE INVENTION

Polymers have served essential needs in society. For many years, these needs were filled by natural polymers. More recently, synthetic polymers have played an increasingly greater role, particularly since the beginning of the 20th century. Especially useful polymers are those prepared by an addition polymerization mechanism, i.e., free radical chain polymerization of unsaturated monomers, and include, by way of example only, coatings and adhesives. In fact, the majority of commercially significant processes is based on free-radical chemistry. That is, chain polymerization is initiated by a reactive species which often is a free radical. The source of the free radicals is termed an initiator or photoinitiator.

Improvements in free radical chain polymerization have focused both on the polymer being produced and the photoinitiator. Whether a particular unsaturated monomer can be converted to a polymer requires structural, thermodynamic, and kinetic feasibility. Even when all three exist, kinetic feasibility is achieved in many cases only with a specific type of photoinitiator. Moreover, the photoinitiator can have a significant effect on reaction rate which, in turn, may determine the commercial success or failure of a particular polymerization process or product.

A free radical-generating photoinitiator may generate free radicals in several different ways. For example, the thermal, homolytic dissociation of an initiator typically directly yields two free radicals per initiator molecule. A photoinitiator, i.e., an initiator which absorbs light energy, may produce free radicals by either of two pathways:

(1) the photoinitiator undergoes excitation by energy absorption with subsequent decomposition into one or more radicals; or (2) the photoinitiator undergoes excitation and the excited species interacts with a second compound (by either energy transfer or a redox reaction) to form free radicals from the latter and/or former compound(s).

While any free radical chain polymerization process should avoid the presence of species which may prematurely terminate the polymerization reaction, prior photoinitiators present special problems. For example, absorption of the light by the reaction medium may limit the amount of energy available for absorption by the photoinitiator. Also, the often competitive and complex kinetics involved may have an adverse effect on the reaction rate. Moreover, commercially available radiation sources, such as medium and high pressure mercury and xenon lamps, emit over a wide wavelength range, thus producing individual emission bands of relatively low intensity. Most photoinitiators only absorb over a small portion of the emission spectra and, as a consequence, most of the lamps' radiation remains unused. In addition, most known photoinitiators have only moderate "quantum yields" (generally less than 0.4) at these wavelengths, indicating that the conversion of light radiation to radical formation can be more efficient.

Thus, there are continuing opportunities for improvements in free radical polymerization photoinitiators. Moreover, there is a need in the art for new, energy-efficient photoinitiators for use in a variety of polymerization and photocuring processes.

SUMMARY OF THE INVENTION

The present invention addresses some of the difficulties and problems discussed above by the discovery of energy-efficient photoinitiators having the following general formula:

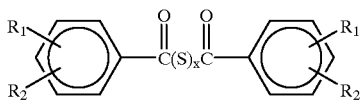

wherein x is an integer from 1 to 4, and $R_1$ and $R_2$ each independently represent H—;

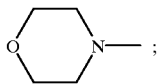

$(R)_2N$— where R is an alkyl group having from one to six carbon atoms; a chalcone; $HSO_3$—; and $NaSO_3$—. In a further embodiment, the present invention is directed to photoinitiators having the following formula:

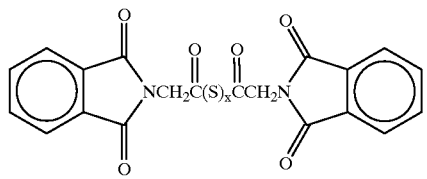

wherein x is an integer from 1 to 4.

The present invention is directed to the above-described photoinitiators, compositions containing the same, and methods for generating a reactive species which includes providing one or more of the photoinitiators and irradiating the one or more photoinitiators. One of the main advantages of the photoinitiators of the present invention is that they efficiently generate one or more reactive species under extremely low energy lamps, such as excimer lamps, as compared to prior art photoinitiators.

The present invention is further directed to methods of using the above-described photoinitiators to polymerize and/or photocure a polymerizable material. The photoinitiators of the present invention result in rapid curing times in comparison to the curing times of prior art photoinitiators, even with relatively low output lamps. The present invention includes a method of polymerizing an unsaturated monomer by exposing the unsaturated monomer to radiation in the presence of the efficacious wavelength specific photoinitiator composition described above. When an unsaturated oligomer/monomer mixture is employed in place of the unsaturated monomer, curing is accomplished.

The present invention further includes a film and a method for producing a film, by drawing an admixture of unsaturated polymerizable material and one or more photoinitiators of the present invention, into a film and irradiating the film with an amount of radiation sufficient to polymerize the composition. The admixture may be drawn into a film on a nonwoven web or on a fiber, thereby providing a polymer-coated nonwoven web or fiber, and a method for producing the same.

The present invention is also directed to an adhesive composition comprising an unsaturated polymerizable material admixed with one or more photoinitiators of the present invention. Similarly, the present invention includes a laminated structure comprising at least two layers bonded together with the above-described adhesive composition, in which at least one layer is a nonwoven web or film. Accordingly, the present invention provides a method of laminating a structure wherein a structure having at least two layers with the above-described adhesive composition between the layers is irradiated to polymerize the adhesive composition.

These and other features and advantages of the present invention will become apparent after a review of the following detailed description of the disclosed embodiments and the appended claims.

DETAILED DESCRIPTION OF THE INVENTION

The present invention is directed to energy-efficient reactive photoinitiators and methods for utilizing the same. More particularly, the present invention is directed to new photoinitiators having the following general formula:

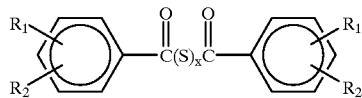

wherein x is an integer from 1 to 4, and $R_1$ and $R_2$ each independently represent H—;

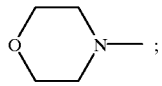

$(R)_2N$— where R is an alkyl group having from one to six carbon atoms; a chalcone; $HSO_3$—; and $NaSO_3$—. In a further embodiment of the present invention, the photoinitiator comprises bis-phthaloylglycine sulfide compounds having the following formula:

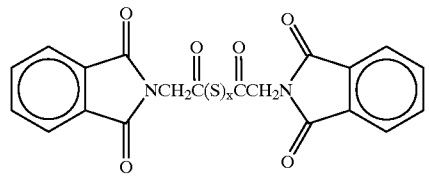

wherein x is an integer from 1 to 4.

The present invention also includes a method of polymerizing an unsaturated polymerizable material by exposing the unsaturated material to radiation in the presence of one or more of the photoinitiators described above. Further, the present invention is directed to a film and a method for producing a film, by drawing an admixture of unsaturated polymerizable material and one or more of the photoinitiators described above, into a film and irradiating the film with an amount of radiation sufficient to polymerize the admixture.

The present invention is further directed to an adhesive composition comprising an unsaturated polymerizable material admixed and one or more photoinitiators of the present invention. Similarly, the present invention includes a laminated structure comprising at least two layers bonded together with the above-described adhesive composition. The present invention further provides a method of laminating a structure wherein a structure having at least two layers with the above-described adhesive composition between the layers is irradiated to polymerize the adhesive composition.

After the following definitions, the photoinitiators of the present invention will be described in detail, followed by a detailed description of the method of generating reactive species, and the various representative applications of the method.

DEFINITIONS

As used herein, the term "reactive species" is used herein to mean any chemically reactive species including, but not limited to, free-radicals, cations, anions, nitrenes, and carbenes. Illustrated below are examples of several of such species. Examples of carbenes include, for example, methylene or carbene, dichlorocarbene, diphenylcarbene, alkylcarbonylcarbenes, siloxycarbenes, and dicarbenes. Examples of nitrenes include, also by way of example, nitrene, alkyl nitrenes, and aryl nitrenes. Cations (sometimes referred to as carbocations or carbonium ions) include, by way of illustration, primary, secondary, and tertiary alkyl carbocations, such as methyl cation, ethyl cation, propyl cation, t-butyl cation, t-pentyl cation, t-hexyl cation; allylic cations; benzylic cations; aryl cations, such as triphenyl cation; cyclopropylmethyl cations; methoxymethyl cation; triarylsulphonium cations; and acyl cations. Cations also include those formed from various metal salts, such as tetra-n-butylammonium tetrahaloaurate(III) salts; sodium tetrachloroaurate(III); vanadium tetrachloride; and silver, copper(I) and (II), and thallium(I) triflates. Examples of anions (sometimes referred to as carbanions) include, by way of example, alkyl anions, such as ethyl anion, npropyl anion, isobutyl anion, and neopentyl anion; cycloalkyl anions, such as cyclopropyl anion, cyclobutyl anion, and cyclopentyl anion; allylic anions; benzylic anions; aryl cations; and sulfur- or phosphorus-containing alkyl anions. Finally, examples of organometallic photoinitiators include titanocenes, fluorinated diaryltitanocenes, iron arene complexes, manganese decacarbonyl, and methylcyclopentadienyl manganese tricarbonyl. Organometallic photoinitiators generally produce free radicals or cations.

As used herein, the term "quantum yield" is used herein to indicate the efficiency of a photochemical process. More particularly quantum yield is a measure of the probability that a particular molecule will absorb a quantum of light during its interaction with a photon. The term expresses the number of photochemical events per photon absorbed. Thus, quantum yields may vary from zero (no absorption) to 1.

As used herein, the term "polymerization" is used herein to mean the combining, e.g. covalent bonding, of large numbers of smaller molecules, such as monomers, to form very large molecules, i.e., macromolecules or polymers. The monomers may be combined to form only linear macromolecules or they may be combined to form three-dimensional macromolecules, commonly referred to as crosslinked polymers.

As used herein, the term "curing" means the polymerization of functional oligomers and monomers, or even polymers, into a crosslinked polymer network. Thus, curing is the polymerization of unsaturated monomers or oligomers in the presence of crosslinking agents.

As used herein, the terms "unsaturated monomer," "functional oligomer," and "crosslinking agent" are used herein with their usual meanings and are well understood by those having ordinary skill in the art. The singular form of each is intended to include both the singular and the plural, i.e., one or more of each respective material.

As used herein, the term "unsaturated polymerizable material" is meant to include any unsaturated material capable of undergoing polymerization. The term encompasses unsaturated monomers, oligomers, and crosslinking agents. Again, the singular form of the term is intended to include both the singular and the plural.

As used herein, the term "fiber" as used herein denotes a threadlike structure. The fibers used in the present invention may be any fibers known in the art. As used herein, the term "nonwoven web" as used herein denotes a web-like matter comprised of one or more overlapping or interconnected fibers in a nonwoven manner. It is to be understood that any nonwoven fibers known in the art may be used in the present invention.

Photoinitiators of the Present Invention

The present invention is directed to new photoinitiators having the following general formula:

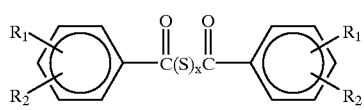

wherein x is an integer from 1 to 4, and $R_1$ and $R_2$ each independently represent H—;

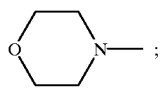

$(R)_2N$— where R is an alkyl group having from one to six carbon atoms; a chalcone; $HSO_3$—; and $NaSO_3$—. In a further embodiment of the present, the photoinitiator comprises bis-m-morpholinobenzoyl trisulfide having the following formula:

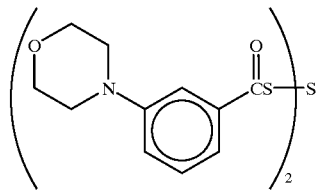

or bis-p-morpholinobenzoyl trisulfide having the following formula:

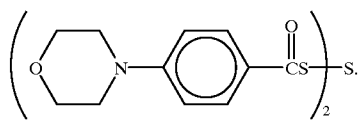

In another embodiment of the present invention, the photoinitiator comprises a bis-dialkylaminobenzoyl trisulfide having the following formula:

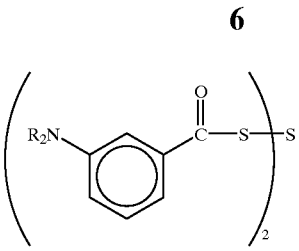

wherein R is an alkyl group having from 1 to 6 carbon atoms. Desirably, the photoinitiator comprises bis-m-dimethylaminobenzoyl trisulfide having the following formula:

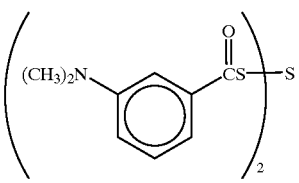

or bis-p-dimethylaminobenzoyl trisulfide having the following formula:

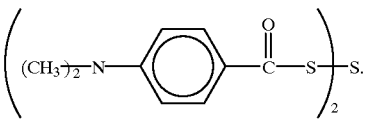

In yet another embodiment of the present invention, the photoinitiator comprises a water-soluble photoinitiator having the following structure:

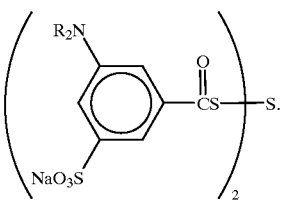

In a further embodiment of the present invention, the photoinitiator comprises bis-phthaloylglycine trisulfide having the following formula:

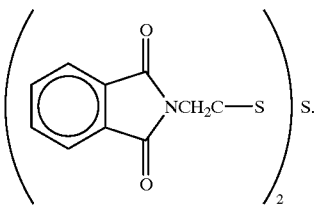

One method of producing the photoinitiators of the present invention is discussed below. However, it should be noted that the photoinitiators of the present invention may be prepared by any reaction mechanism known to those of ordinary skill in the art. In one embodiment of the present invention, special reagents, used to prepare the photoinitiators of the present invention, are produced by reacting sulfur with a desired amount of lithium triethylborohydride to produce lithium sulfide compounds. The above-described reaction is shown by the following mechanism:

$$2Li(CH_3)_3BH + {}_yS \rightarrow Li_2S_y$$

Various lithium sulfide compounds may be produced by the above-described reaction including, but not limited to, $Li_2S$, $Li_2S_2$, and $Li_2S_3$. Preferably y is an integer from 1 to 4. The above-described reaction results in a variety of lithium sulfide compounds wherein y varies from 1 to 3. However, these compounds may be separated using separation techniques known to those of ordinary skill in the art if desired.

The lithium sulfide compounds may be further reacted with a substituted benzoyl chloride, a phthaloylglycine chloride or other carbonyl chloride compounds to produce one or more photoinitiators of the present invention. In one embodiment of the present invention, a morpholinobenzoyl chloride is reacted with one or more lithium sulfide compounds to produce one or more morpholinobenzoyl sulfide compounds. In a further embodiment of the present invention, phthaloylglycine chloride is reacted with one or more lithium sulfide compounds to produce one or more phthaloylglycine sulfide compounds.

The resulting photoinitiators are stable at room temperature (from about 15° C. to 25° C.) and normal room humidity (from about 30% to 60%). However, upon exposure to radiation, the photoinitiators efficiently produce one or more free radicals. The photoinitiators of the present invention have a high intensity of absorption. For example, the photoinitiators of the present invention may have a molar extinction coefficient greater than about 2,000 liters per mole per cm (1 $mole^{-1}cm^{-1}$) at an absorption maximum. As another example, the photoinitiators of the present invention may have a molar extinction coefficient (absorptivity) greater than about 5,000 1 $mole^{-1}cm^{-1}$. As another example, the photoinitiators of the present invention may have a molar extinction coefficient (absorptivity) greater than about 10,000 1 $mole^{-1}cm^{-1}$. As a further example, the photoinitiators of the present invention will have a molar extinction coefficient greater than about 20,000 1 $mole^{-1}$ $cm^{-1}$.

Method of Generating a Reactive Species and Applications Therefor

The present invention is also directed to a method of generating a reactive species. The method of generating a reactive species involves generating a reactive species by exposing one or more of the above-described photoinitiators to radiation. The exposure of the photoinitiators to a radiation source triggers a photochemical process. As stated above, the term "quantum yield" is used herein to indicate the efficiency of a photochemical process. More particularly, quantum yield is a measure of the probability that a particular molecule (photoinitiator) will absorb a quantum of light during its interaction with a photon. The term expresses the number of photochemical events per photon absorbed. Thus, quantum yields may vary from zero (no absorption) to 1.

The photoinitiators of the present invention absorb photons having a specific wavelength and transfers the absorbed energy to one or more excitable portions of the molecule. The excitable portion of the molecule absorbs enough energy to cause a bond breakage, which generates one or more reactive species. The efficiency with which a reactive species is generated with the photoinitiators of the present invention is significantly greater than that experienced with photoinitiators of the prior art as indicated by faster cure times. For example, the photoinitiators of the present invention desirably will have a quantum yield greater than about 0.5. More desirably, the quantum yield of the photoinitiators of the present invention will be greater than about 0.6. Even more desirably, the quantum yield of the photoinitiators of the present invention will be greater than about 0.7. Still more desirably, the quantum yield of the photoinitiators of the present invention will be greater than about 0.8, with the most desirable quantum yield being greater than about 0.9.

Exposing the photoinitiators of the present invention to radiation results in the generation of one or more reactive species. Thus, the photoinitiators may be employed in any situation where reactive species are required, such as for the polymerization of an unsaturated monomer and the curing of an unsaturated oligomer/monomer mixture. The unsaturated monomers and oligomers may be any of those known to one having ordinary skill in the art. In addition, the polymerization and curing media also may contain other materials as desired, such as pigments, extenders, amine synergists, and such other additives as are well known to those having ordinary skill in the art.

By way of illustration only, examples of unsaturated monomers and oligomers include ethylene, propylene, vinyl chloride, isobutylene, styrene, isoprene, acrylonitrile, acrylic acid, methacylic acid, ethyl acrylate, methyl methacrylate, vinyl acrylate, allyl methacrylate, tripropylene glycol diacrylate, trimethylol propane ethoxylate acrylate, epoxy acrylates, such as the reaction product of a bisphenol A epoxide with acrylic acid; polyester acrylates, such as the reaction product of acrylic acid with an adipic add/hexanediol-based polyester, urethane acrylates, such as the reaction product of hydroxypropyl acrylate with diphenylmethane-4,4'-diisocyanate, and polybutadiene diacrylate oligomer.

The types of reactions that various reactive species enter into include, but are not limited to, addition reactions, including polymerization reactions; abstraction reactions; rearrangement reactions; elimination reactions, including decarboxylation reactions; oxidation-reduction (redox) reactions; substitution reactions; and conjugation/deconjugation reactions.

Accordingly, the present invention also comprehends a method of polymerizing an unsaturated monomer by exposing the unsaturated monomer to radiation in the presence of the efficacious photoinitiators of the present invention described above. When an unsaturated oligomer/monomer mixture is employed in place of the unsaturated monomer, curing is accomplished. It is to be understood that the polymerizable material admixed with the photoinitiators of the present invention is to be admixed by means known in the art, and that the mixture will be irradiated with an amount of radiation sufficient to polymerize the material. The amount of radiation sufficient to polymerize the material is readily determinable by one of ordinary skill in the art, and depends upon the identity and amount of photoinitiators, the identity and amount of the polymerizable material, the intensity and wavelength of the radiation, and the duration of exposure to the radiation.

It is believed that radiation exposure results in the generation of free radicals from the photoinitiators of the present invention by one or more of the following: cleavage of a sulfur-sulfur bond resulting in two sulfur-terminated free radicals; and cleavage of a carbon-sulfur bond resulting in a carbon-terminated free radical and a sulfur-terminated free radical.

Polymer Films, Coated Fibers and Webs, and Adhesive Compositions

The present invention further includes a film and a method for producing a film, by drawing an admixture of unsaturated polymerizable material and one or more photoinitiators of the present invention, into a film and irradiating the film with an amount of radiation sufficient to polymerize the composition. When the unsaturated polymerizable material is an unsaturated oligomer/monomer mixture, curing is accomplished. Any film thickness may be produced, as per the thickness of the admixture formed, so long as the admixture sufficiently polymerizes upon exposure to radiation. The admixture maybe drawn into a film on a nonwoven web or on a fiber, thereby providing a polymer-coated nonwoven web or fiber, and a method for producing the same. Any method known in the art of drawing the admixture into a film may be used in the present invention. The amount of radiation sufficient to polymerize the material is readily determinable by one of ordinary skill in the art, and depends upon the identity and amount of photoinitiator, the identity and amount of the polymerizable material, the thickness of the admixture, the intensity and wavelength of the radiation, and duration of exposure to the radiation.

The present invention also includes an adhesive composition comprising an unsaturated polymerizable material admixed with one or more photoinitiators of the present invention. Similarly, the present invention includes a laminated structure comprising at least two layers bonded together with the above-described adhesive composition. In one embodiment of the present invention, a laminate is produced wherein at least one layer is a cellulosic or polyolefin nonwoven web or film. Accordingly, the present invention provides a method of laminating a structure wherein a structure having at least two layers with the above-described adhesive composition between the layers is irradiated to polymerize the adhesive composition. When the unsaturated polymerizable material in the adhesive is an unsaturated oligomer/monomer mixture, the adhesive is irradiated to cure the composition.

It is to be understood that any layers may be used in the laminates of the present invention, on the condition that at least one of the layers allows sufficient radiation to penetrate through the layer to enable the admixture to polymerize sufficiently. Accordingly, any cellulosic or polyolefin nonwoven web or film known in the art may be used as one of the layers so long as they allow radiation to pass through. Again, the amount of radiation sufficient to polymerize the admixture is readily determinable by one of ordinary skill in the art, and depends upon the identity and amount of photoinitiator, the identity and amount of the polymerizable material, the thickness of the admixture, the identity and thickness of the layer, the intensity and wavelength of the radiation, and the duration of exposure to the radiation.

The radiation to which the photoinitiators of the present invention may be exposed generally will have a wavelength of from about 4 to about 1,000 nanometers. Thus, the radiation may be ultraviolet radiation, including near ultraviolet and far or vacuum ultraviolet radiation; visible radiation; and near infrared radiation. Desirably, the radiation will have a wavelength of from about 100 to about 900 nanometers. More desirably, the radiation will have a wavelength of from about 100 to 700 nanometers. Desirably, the radiation will be ultraviolet radiation having a wavelength of from about 4 to about 400 nanometers. More desirably, the radiation will have a wavelength of from about 100 to about 390 nanometers, and even more desirably will have a wavelength of from 200 to about 380 nanometers. For example, the radiation may have a wavelength of from about 222 to about 370 nanometers. The radiation desirably will be incoherent, pulsed ultraviolet radiation from a dielectric barrier discharge excimer lamp or radiation from a mercury lamp.

Excimers are unstable excited-state molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. The dielectric barrier excimers in general emit in the range of from about 125 nm to about 500 nm, depending upon the excimer gas mixture.

Dielectric barrier discharge excimer lamps (also referred to hereinafter as "excimer lamp") are described, for example, by U. Kogelschatz, "Silent discharges for the generation of ultraviolet and vacuum ultraviolet excimer radiation." Pure & Appl. Chem., 62, No. 9, pp. 16671674 (1990); and E. Eliasson and U. Kogelschatz, "UV Excimer Radiation from Dielectric-Barrier Discharges." Appl. Phys. B. 46, pp. 299–303 (1988). Excimer lamps were developed by ABB Infocom Ltd., Lenzburg, Switzerland, and at the present time are available from Heraeus Noblelight GmbH, Kleinostheim, Germany.

The excimer lamp emits incoherent, pulsed ultraviolet radiation. Such radiation has a relatively narrow bandwidth, i.e., the half width is of the order of approximately 5 to 100 nanometers. Desirably, the radiation will have a half width of the order of approximately 5 to 50 nanometers, and more desirably will have a half width of the order of 5 to 25 nanometers. Most desirably, the half width will be of the order of approximately 5 to 15 nanometers.

The ultraviolet radiation emitted from an excimer lamp can be emitted in a plurality of wavelengths, wherein one or more of the wavelengths within the band are emitted at a maximum intensity. Accordingly, a plot of the wavelengths in the band against the intensity for each wavelength in the band produces a bell curve. The "half width" of the range of ultraviolet radiation emitted by an excimer lamp is defined as the width of the bell curve at 50% of the maximum height of the bell curve.

The emitted radiation of an excimer lamp is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification and the claims. Thus, in comparison with most other commercially useful sources of ultraviolet radiation which typically emit over the entire ultraviolet spectrum and even into the visible region, excimer lamp radiation is essentially monochromatic.

The source of radiation used with the photoinitiators of the present invention may be any radiation source known to those of ordinary skill in the art. In one embodiment of the present invention, a mercury lamp with a D-bulb, which produces radiation having an emission peak of 350 nm is used to produce free radicals from the above-described photoinitiators. This radiation source is particularly useful when matched with one or more photoinitiators of the present invention having an absorption maximum of 350 nanometers, corresponding to the emission peak of the mercury lamp.

As a result of the photoinitiators of the present invention absorbing radiation in the range of about 250 to about 350 nanometers, the photoinitiators of the present invention will generate one or more reactive species upon exposure to sunlight. Accordingly, these photoinitiators of the present invention provides a method for the generation of reactive species that does not require the presence of a special light source.

The photoinitiators of the present invention enable the production of adhesive and coating compositions that consumers can apply to a desired object and polymerize or cure upon exposure to sunlight. These photoinitiators also enable numerous industry applications wherein unsaturated polymerizable materials may be polymerized merely upon exposure to sunlight. Therefore, depending upon how the photoinitiator is designed, the photoinitiator of the present invention can eliminate the cost of purchasing and maintaining light sources in numerous industries wherein such light sources are necessary without the photoinitiators of the present invention.

The effective tuning of the photoinitiators of the present invention for a specific wavelength band permits the photoinitiators of the present invention to more efficiently utilize the target radiation in the emission spectrum of the radiating source corresponding to the "tuned" wavelength band, even though the intensity of such radiation may be much lower than, for example, radiation from a narrow band emitter, such as an excimer lamp. For example, it may be desirable to utilize an excimer lamp, or other radiation emission source, that emits radiation having a wavelength of approximately 222 nm with the phthaloylglycine-containing photoinitiators of the present invention. Similarly, it may be desirable to utilize a mercury lamp that emits radiation having a wavelength of approximately 350 nm with the substituted benzoyl-containing photoinitiators of the present invention. However, the effectiveness of the photoinitiators of the present invention is not necessarily dependent upon the availability or use of a narrow wavelength band radiation source.

Accordingly, a major advantage of the photoinitiators of the present invention is that they have rapid curing times in comparison to the curing times of the prior art. Another advantage of the present invention is that the photoinitiators of the present invention are highly sensitive photoinitiators and are beneficially used in situations having lower light levels.

The present invention is further described by the examples which follow. Such examples, however, are not to be construed as limiting in any way either the spirit or the scope of the present invention. In the examples, all parts are by weight, unless stated otherwise.

EXAMPLE 1

Preparation of 3-morpholinobenzoic Acid

This example describes a method of synthesizing the following compound, 3-morpholinobenzoic acid, which is used in the reaction mechanism for preparing bis-m-morpholinobenzoyl trisulfide:

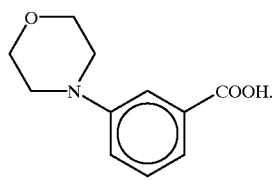

The reaction proceeded as shown below:

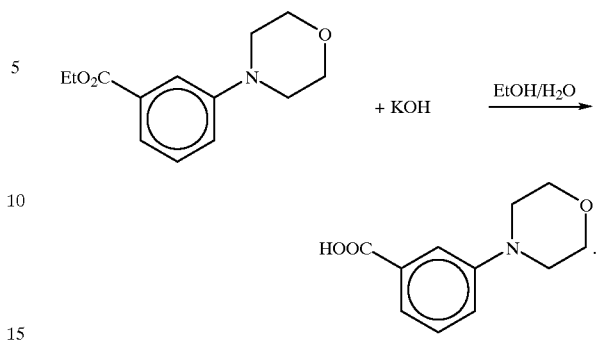

4.3 g of KOH was dissolved in 200 milliliters of ethanol and 100 milliliters of water. Then 5.0 g of 3-morpholinobenzoic acid ester was added and the mixture stirred while heated at reflux for about 2 hours. The mixture was neutralized with dilute HCL and subsequently filtered to give a white solid. The white solid was dried by a Dean & Stark apparatus using toluene to remove the water. The reaction yielded 4.4 g of a white powder, 3-morpholinobenzoic acid.

EXAMPLE 2

Preparation of 3-morpholinobenzoyl Chloride

This example describes a method of synthesizing the following compound, 3-morpholinobenzoyl chloride, which is used as a reactant to form bis-m-morpholinobenzoyl trisulfide:

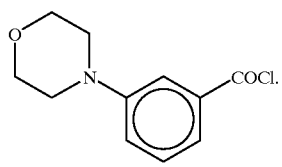

The reaction proceeded as shown below:

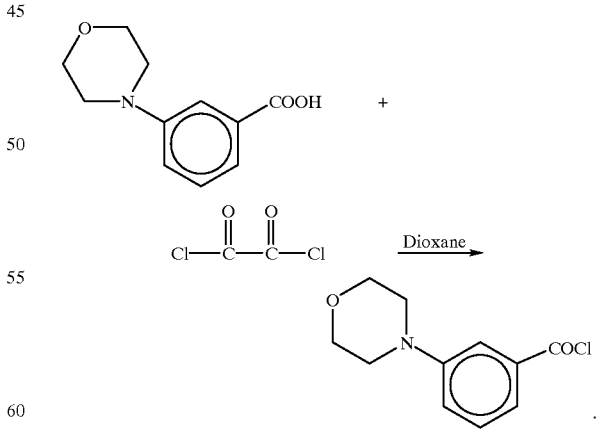

The above reagents, including 25 g of 3-morpholinobenzoic acid and 15.2 g of oxalyl chloride, were mixed in dioxane at 0° C. under argon gas. The reaction proceeded for about 2 hours, one hour at 0° C. and one hour at room temperature. The solvent was then removed under reduced pressure to yield 22.1 g of 3-morpholinobenzoyl chloride, which was used without further purification.

EXAMPLE 3

Preparation of bis-m-morpholinobenzoyl Trisulfide

This example describes a method of synthesizing the following compound, bis-m-morpholinobenzoyl trisulfide:

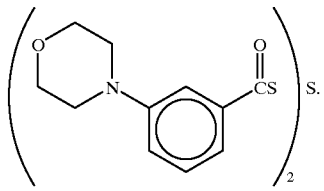

The reaction proceeded as shown below:

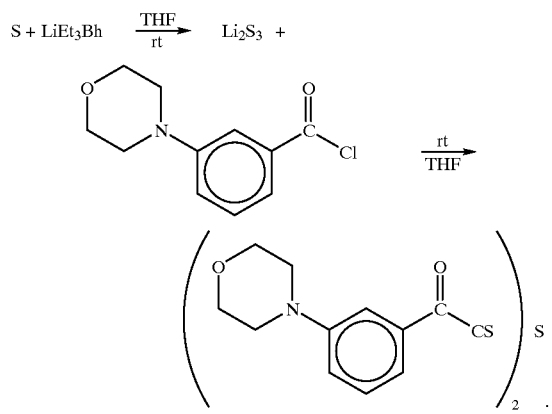

In the first step of the above reaction, 0.1 g of sulfur was added to a 100 ml three-neck flask with magnetic stirrer bar and flushed with argon. 20 ml of 1M lithium triethylborohydride was slowly added to the flask. The reactants were mixed at room temperature in tetrahydrofuran (THF) for about 30 minutes resulting in a pale yellow solution. To this solution was added 50 ml of THF followed by 4.4 g of 3-morpholinobenzoyl chloride. The solution turned a deep yellow/red color and was allowed to stir at room temperature for about one hour. After about one hour, the mixture had become a thick paste with a yellow color.

The reaction product was filtered to yield a yellow solid which was washed with water, benzene, and subsequently dried under vacuum. The reaction yielded 3.4 g of bis-m-morpholinobenzoyl trisulfide.

The reaction HPLC showed complete reaction after about 30 minutes, yielding two products with retention times respectively of about 10 and about 15 minutes in a ratio of about 25:75. The 75% peak was the bis-m-morpholinobenzoyl trisulfide solid while the 25% peak was in the filtrated liquid.

EXAMPLE 4

Photocuring of bis-m-morpholinobenzoyl Trisulfide in Red Flexo Resin

A 2% wt/wt mixture of bis-m-morpholinobenzoyl trisulfide powder was added to a 1 g sample of red flexo ink (Gamma Graphics). The solubility was poor at room temperature; however, the solubility improved upon heating the mixture on a hot plate. A drop of the mixture was placed on a metal plate and drawn down with a zero bar. The thin film was exposed to a brief flash of a D-bulb lamp (Fusion Systems). The thin film was instantly cured.

Another thin film sample was cured using a medium pressure mercury lamp. The mercury lamp has a good emission at a wavelength of 350 nm. Exposure of less than one second resulted in full curing of the thin film.

EXAMPLE 5

Preparation of p-morpholinobenzoyl Ester

The formation of p-morpholinobenzoyl ester was conducted by the following reaction:

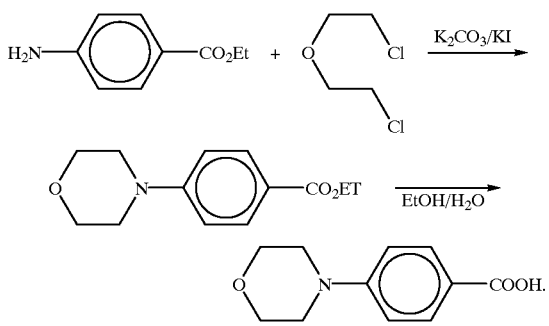

The above reagents, including 100 g of ethyl 4-aminobenzoic acid ester and 114 g of oxalyl chloride, were placed in a three liter round-bottom flask with condenser and mechanical stirrer. The reaction mixture was stirred at reflux for 15 hours. The hot solution was filtered to remove the solvent and yield a white solid. The white solid was recrystallized in benzene to yield 100 g of a white crystalline solid, p-morpholinobenzoyl ester.

EXAMPLE 6

Hydrolysis of p-morpholinobenzoyl Ester

The hydrolysis of p-morpholinobenzoyl ester proceeded as shown in the following reaction:

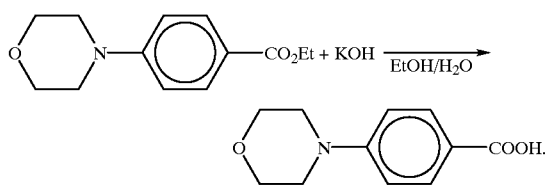

15.2 g of KOH was dissolved in 200 milliliters of ethanol and 100 milliliters of water. To the mixture was added 80 g of p-morpholinobenzoyl ester. The mixture was stirred at room temperature overnight. The mixture was neutralized with dilute HCL and subsequently filtered to give a white solid. The white solid was dried by a Dean and Stark apparatus using toluene to remove the water. The reaction yielded 65 g of 4-morpholinobenzoic acid.

EXAMPLE 7

Preparation of 4-morpholinobenzoyl Chloride

The preparation of 4-morpholinobenzoyl chloride was conducted using the following reaction:

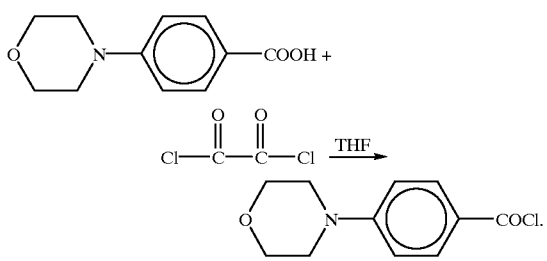

A solution was formed with 60 g of 4-morpholinobenzoic acid in toluene at 0° C. To the solution was added 28.5 g of oxalyl chloride in 50 milliliters of THF over a period of about 10 minutes. The reaction mixture was stirred at 0° C. for about 1 hour followed by stirring at room temperature for about 2 hours. The solution was filtered and the solvent removed under reduced pressure to yield a white solid. The reaction yielded 58.2 g of 4-morpholinobenzoyl chloride, which was used in subsequent reactions without further purification.

EXAMPLE 8

Preparation of bis-p-morphobenzoyl Trisulfide

The preparation of bis-p-morphobenzoyl trisulfide proceeded as shown in the following reaction:

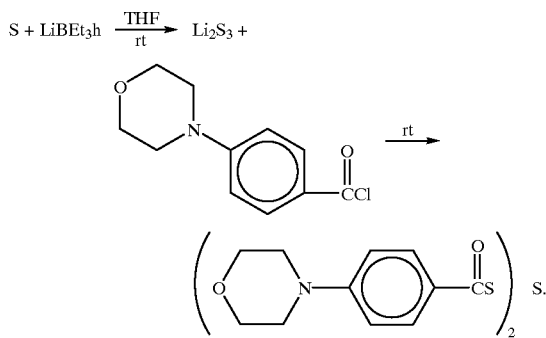

In a 250 milliliter round bottom flask fitted with a condenser and a magnetic stir bar, and flushed with argon gas was added 1 g of sulfur. To the sulfur was added 20 ml of lithium triethylborohydride by using a syringe over a period of about 3 minutes. The mixture was stirred at room temperature for 30 minutes, after which time, the mixture had stopped bubbling ($H_2$ evolution). The color of the solution turned from red to pale yellow. To the mixture was added 4.4 g of 4-morpholinobenzoyl chloride over a period about 5 minutes. The reaction mixture was stirred for about 1 hour. The reaction mixture was filtered to separate a yellow filtrate, which was subsequently washed with toluene and dried under vacuum. The yellow solid was recrystallized from acetonitrile to yield 2.1 g of bis-p-morpholinobenzoyl trisulfide.

EXAMPLE 9

Photocuring bis-p-morpholinobenzoyl Trisulfide in Red Flexo Resin

A 2% wt/wt mixture of bis-p-morpholinobenzoyl trisulfide and 1.0 g of red flexo resin (Gamma Graphics) was mixed for about 5 minutes while stirring at a temperature of about 30 to 40° C. A drop of the mixture was placed on a metal plate and drawn down with a 0 bar. The resulting film was exposed to radiation from a medium pressure mercury lamp for approximately 0.1 seconds to fully cure the film.

EXAMPLE 10

Preparation of bis-p-dimethylaminobenzoyl Chloride

The preparation of bis-p-dimethylaminobenzoyl chloride proceeded as shown in the following reaction:

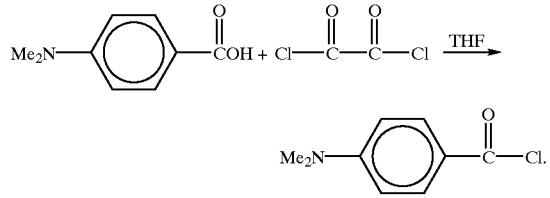

To a solution of 60 g of p-dimethylaminobenzoic acid in toluene at 0° C. was slowly added 46.1 g of oxalyl chloride and 50 milliliters of THF for a period of about 10 minutes. The mixture was stirred at 0° C. for about 1 hour followed by stirring at room temperature for about 2 hours. The mixture was filtered to remove the solvent and yield 62 g of a solid, bis-p-dimethylaminobenzoyl chloride. The solid was used in the following examples without further purification.

EXAMPLE 11

Preparation of bis-p-dimethylaminobenzoyl Trisulfide

The preparation of bis-p-dimethylaminobenzoyl trisulfide proceeded as shown in the following reaction:

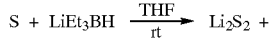
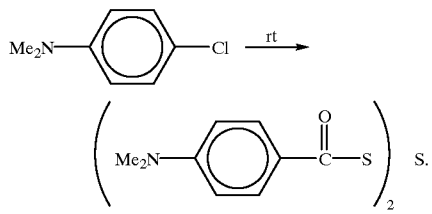

In a 250 ml round-bottom flask fitted with condenser and magnetic stir bar, and flushed with argon gas, was added 1 g of sulfur. To the sulfur was added 20 ml of a 1M solution of lithium triethylborohydride over a period of about 3 minutes by syringe. The mixture was stirred at room temperature for about 30 minutes. To the mixture was added 3.7 g of p-dimethylaminobenzoyl chloride over a period of about 5 minutes. The mixture was stirred for about 1 hour and subsequently filtered to remove a yellow solid. The yellow solid was washed with toluene and subsequently dried to yield 2.1 g of bis-p-dimethylaminobenzoyl trisulfide. HPLC of the reaction showed one product having a retention time of about 15 minutes at a maximum wavelength of 360 nm.

EXAMPLE 12

Photocuring of bis-p-dimethylaminobenzoyl Trisulfide in Red Flexo Resin

A 2% wt/wt. mixture of p-dimethylaminobenzoyl trisulfide and 1.0 g of red flexo resin (Gamma Graphics) was mixed for about 5 minutes while stirring at a temperature of about 30 to 40° C. A drop of the mixture was placed on a metal plate and drawn down with a 0 bar. The resulting film was exposed to radiation from a medium pressure mercury lamp for approximately 0.1 seconds to fully cure the film.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A photoinitiator having the following formula:

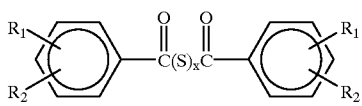

wherein x is an integer from 1 to 4, and $R_1$ and $R_2$ each independently represent H—

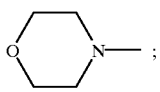

$(R)_2N$— where R is an akyl group having from one to six carbon atoms; a chalcone; $HSO_3$— or $NaSO_3$—; wherein at least oen of $R_1$ and $R_2$ is not H—.

2. A photoinitiator having the following formula:

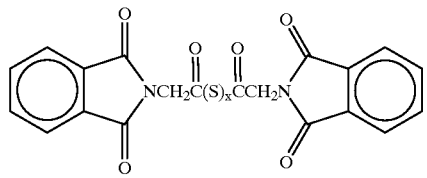

wherein x is an integer from 1 to 4.

3. A method of generating a reactive species, comprising irradiating the photoinitiator of claim 1 with radiation.

4. A method of generating a reactive species, comprising irradiating the photoinitiator of claim 2 with radiation.

5. A method of polymerizing an unsaturated polymerizable material, comprising irradiating an admixture of an unsaturated polymerizable material and the photoinitiator of claim 1.

6. A method of polymerizing an unsaturated polymerizable material, comprising irradiating an admixture of an unsaturated polymerizable material and the photoinitiator of claim 2.

7. A polymer film, produced by the process of:
providing an admixture of an unsaturated polymerizable material and the photoinitiator of claim 1 that has been drawn into a film; and
irradiating the film with an amount of radiation sufficient to polymerize the admixture.

8. A polymer film, produced by the process of:
providing an admixture of an unsaturated polymerizable material and the photoinitiator of claim 2 that has been drawn into a film; and
irradiating the film with an amount of radiation sufficient to polymerize the admixture.

9. A method of coating a nonwoven web comprising:
providing a nonwoven web coated with an admixture of unsaturated polymerizable material and the photoinitiator of claim 1; and
irradiating the coating on the web with an amount of radiation sufficient to polymerize the admixture.

10. A method of coating a nonwoven web comprising:
providing a nonwoven web coated with an admixture of unsaturated polymerizable material and the photoinitiator of claim 2; and
irradiating the coating on the web with an amount of radiation sufficient to polymerize the admixture.

11. A method of coating a fiber comprising:
providing a fiber coated with an admixture of unsaturated polymerizable material and the photoinitiator of claim 1; and
irradiating the coating on the fiber with an amount of radiation sufficient to polymerize the admixture.

12. A method of coating a fiber comprising:
providing a fiber coated with an admixture of unsaturated polymerizable material and the photoinitiator of claim 2; and
irradiating the coating on the fiber with an amount of radiation sufficient to polymerize the admixture.

13. The photoinitiator of claim 1, wherein the photoinitiator has the following formula:

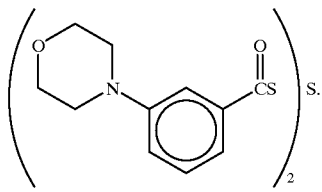

14. The photoinitiator of claim 1, wherein the photoinitiator has the following formula:

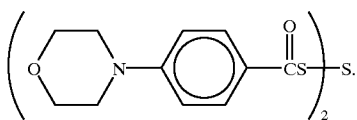

15. The photoinitiator of claim 1, wherein the photoinitiator has the following formula:

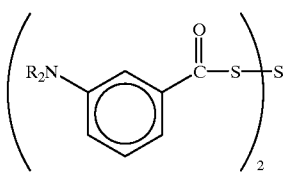

wherein R is an alkyl group having from 1 to 6 carbon atoms.

16. The photoinitiator of claim 15, wherein the photoinitiator has the following formula:

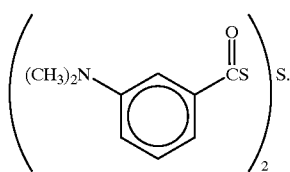

17. The photoinitiator of claim 1, wherein the photoinitiator has the following formula:

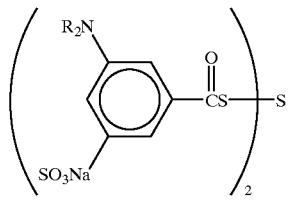

wherein R is an alkyl group having from 1 to 6 carbon atoms.

18. The photoinitiator of claim 2, wherein the photoinitiator has the following formula:

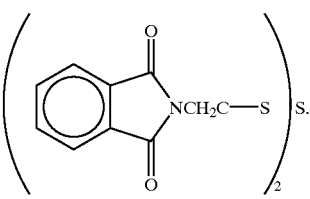

19. The photoinitiator of claim 1, wherein $R_1$ and $R_2$ each independently represent

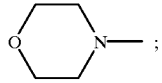

$(R)_2N$— where R is an alkyl group having from one to six carbon atoms; a chalcone; $HSO_3$— or $NaSO_3$—.

20. The photoinitiator of claim 1, wherein at least one of $R_1$ and $R_2$ represent

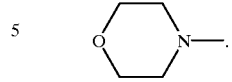

21. The photoinitiator of claim 1, wherein at least one of $R_1$ and $R_2$ represent $(R)_2N$— where R is an alkyl group having from one to six carbon atoms.

22. The photoinitiator of claim 1, wherein at least one of $R_1$ and $R_2$ represent a chalcone.

23. The photoinitiator of claim 1, wherein at least one of $R_1$ and $R_2$ represent $HSO_3$—.

24. The photoinitiator of claim 1, wherein at least one of $R_1$ and $R_2$ represent $NaSO_3$—.

25. A photoinitiator having the following formula:

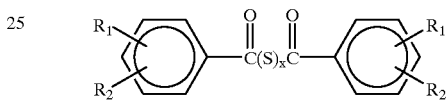

wherein x is an integer from 1 to 4; and wherein $R_1$ and $R_2$ each independently represent

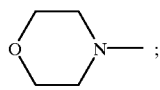

$(R)_2N$— where R is an alkyl group having from one to six carbon atoms; a chalcone; $HSO_3$— or $NaSO_3$—.

* * * * *